(12) United States Patent
Filvaroff et al.

(10) Patent No.: US 12,357,633 B2
(45) Date of Patent: Jul. 15, 2025

(54) METHODS OF TREATING CANCER BY TARGETING COLD TUMORS

(71) Applicant: Celgene Corporation, Summit, NJ (US)

(72) Inventors: Ellen Filvaroff, Summit, NJ (US); Brian Fox, Summit, NJ (US); Ida Aronchik, Summit, NJ (US); Tracy Chow, Summit, NJ (US)

(73) Assignee: Celgene Corporation, Summit, NJ (US)

( * ) Notice: Subject to any disclaimer, the term of this patent is extended or adjusted under 35 U.S.C. 154(b) by 847 days.

(21) Appl. No.: 17/618,415

(22) PCT Filed: Jun. 12, 2020

(86) PCT No.: PCT/US2020/037521
§ 371 (c)(1),
(2) Date: Dec. 10, 2021

(87) PCT Pub. No.: WO2020/252331
PCT Pub. Date: Dec. 17, 2020

(65) Prior Publication Data
US 2022/0273654 A1 Sep. 1, 2022

Related U.S. Application Data

(60) Provisional application No. 62/861,094, filed on Jun. 13, 2019.

(51) Int. Cl.
*A61K 31/506* (2006.01)
*A61K 31/365* (2006.01)
*A61K 31/555* (2006.01)
*C07K 16/28* (2006.01)

(52) U.S. Cl.
CPC .......... *A61K 31/506* (2013.01); *A61K 31/365* (2013.01); *A61K 31/555* (2013.01); *C07K 16/2818* (2013.01); *C07K 16/2827* (2013.01)

(58) Field of Classification Search
CPC .. A61K 31/506; A61K 31/365; A61K 31/555; C07K 16/2818; C07K 16/2827
See application file for complete search history.

(56) References Cited

U.S. PATENT DOCUMENTS

| | | |
|---|---|---|
| 9,255,097 B2 | 2/2016 | Chen et al. |
| 9,573,930 B2 | 2/2017 | Chen et al. |
| 9,771,329 B2 | 9/2017 | Chen et al. |
| 10,328,077 B2 | 6/2019 | Xu et al. |
| 2018/0319767 A1 | 11/2018 | Chen et al. |
| 2019/0000831 A1 | 1/2019 | Liau et al. |

FOREIGN PATENT DOCUMENTS

| | | | | |
|---|---|---|---|---|
| CN | 109803660 A | 5/2019 | | |
| WO | WO-2014205266 A2 * | 12/2014 | ........... | A61K 31/135 |
| WO | WO 2015/168466 | 11/2015 | | |
| WO | WO-2017/079670 A1 | 5/2017 | | |
| WO | WO-2018/031658 A1 | 2/2018 | | |
| WO | WO-2018106984 A1 * | 6/2018 | ............. | A61K 31/13 |
| WO | WO-2019083971 A1 * | 5/2019 | ........... | A61K 31/445 |

OTHER PUBLICATIONS

Majello, et al., "Expanding the Role of the Histone Lysine-Specific Demethylase LSD1 in Cancer," Cancers, vol. 11, No. 324, 15 pages (2019).
Mauldin, et al., "TLR2/6 Agonists and IFNy Synergize to Induce Melanoma Cells to Produce T-cell recruiting chemokines," Journ. of ImmunoTherapy of Cancer, vol. 1 (Suppl), 1 page (Nov. 2013).
Search Report issued in European Patent Application No. 20822351. 1, dated May 10, 2023.
Sheng et al., "LSD1 Ablation Stimulates Anti-Tumor Immunity and Enables Checkpoint Blockade," Cell, vol. 174, pp. 549-563 (Jul. 2018).
Streicher, et al., "Gene Expression Analysis of Tumor Biopsies from a Trial of Durvalumab to Identify Subsets of NSCLC with shared immune pathways," Journal. of Clinical Oncology, vol. 35, No. 15, (May 20, 2017) [Abstract].
Vonderheide, "The Immune Revolution: A Case for Priming, Not Checkpoint," Cancer Cell, vol. 33, pp. 563-569 (Apr. 2018).
Office Action issued in Chinese Patent Application No. 202080056280.1 dated May 30, 2023.
Fares et al., "Mechanisms of Resistance to Immune Checkpoint Blockade: Why Does Checkpoint Inhibitor Immunotherapy Not Work for All Patients?," American Society of Clinical Oncology Educational Book, vol. 39, pp. 147-164 (2019).
Ramos et al., "Mechanisms of Resistance to Immune Checkpoint Antibodies," Handb. Exp. Pharmacol., vol. 249, pp. 109-128 (2017).
Barbie et al., "Systematic RNA interference reveals that oncogenic KRAS-driven cancers require TBK1," Nature, vol. 462, pp. 108-112 (2009).
Hanzelmann et al., "GSVA: gene set variation analysis for microarray and RNA-Seq. data." BMC Bioinformatics, vol. 14, No. 7, pp. 1-15 (2013).
Berge, et al., "Pharmaceutical Salts," J. Pharma. Sci., vol. 66, pp. 1-19 (1997).
Fernandez, et al., "Cancer-Specific Thresholds Adjust for Whole Exome Sequencing-Based Tumor Mutational Burden Distribution," American Society of Clinical Oncology, 12 pages (2019).
Yang, et al., "Pharmacological Inhibition of LSD1 for Cancer Treatment," Molecules, vol. 23, No. 3194, 20 pages (2018).

(Continued)

Primary Examiner — Kortney L. Klinkel
Assistant Examiner — Donna M Nestor
(74) Attorney, Agent, or Firm — Foley & Lardner LLP

(57) ABSTRACT

Methods are provided for the treatment of cancer or neoplastic diseases and the like, by administering 4-[2-(4-amino-piperidin-1-yl)-5-(3-fluoro-4-methoxy-phenyl)-1-methyl-6-oxo-1,6-dihydro-pyrimidin-4-yl]-2-fluoro- benzonitrile (compound of Formula (I)) or a pharmaceutically acceptable salt thereof, and pharmaceutical compositions comprising compounds useful for the inhibition of lysine specific demethylase-1 (LSD-1) to patients in need thereof. Methods are further drawn to administering compositions described herein to patients having neoplastic cells that express RCOR2.

22 Claims, 15 Drawing Sheets

(56) References Cited

OTHER PUBLICATIONS

Maiques-Diaz, et al., "LSD1: Biologic Roles and Therapeutic Targeting," *Epigenomics*, vol. 8, No. 8, pp. 1103-1116 (2016).
Mater, et al., "Management of Recurrent Ewing Sarcoma: Challenges and Approaches," *Onco Targets and Therapy*, vol. 12, pp. 2279-2288 (2019).
International Search Report and Written Opinion issued in International Patent Application No. PCT/US2020/037521, dated Oct. 29, 2020.
Office Action for Eurasia Patent Application No. 202193252, dated Dec. 17, 2023.
Qin et al., "Inhibition of histone lysine-specific demethylase 1 elicits breast tumor immunity and enhances antitumor efficacy of immune checkpoint blockade," Oncogene, Jan. 2019, vol. 38, No. 3 (pp. 390-405).
Search Report and Written Opinion for Singapore Patent Application No. 11202113758Y, dated Dec. 25, 2023.
Sweis et al., "Molecular Drivers of the Non-T-cell-Inflamed Tumor Microenvironment in Urothelial Bladder Cancer," Cancer Immunology Research, Jul. 2016, vol. 4, No. 7 (pp. 563-568).

* cited by examiner

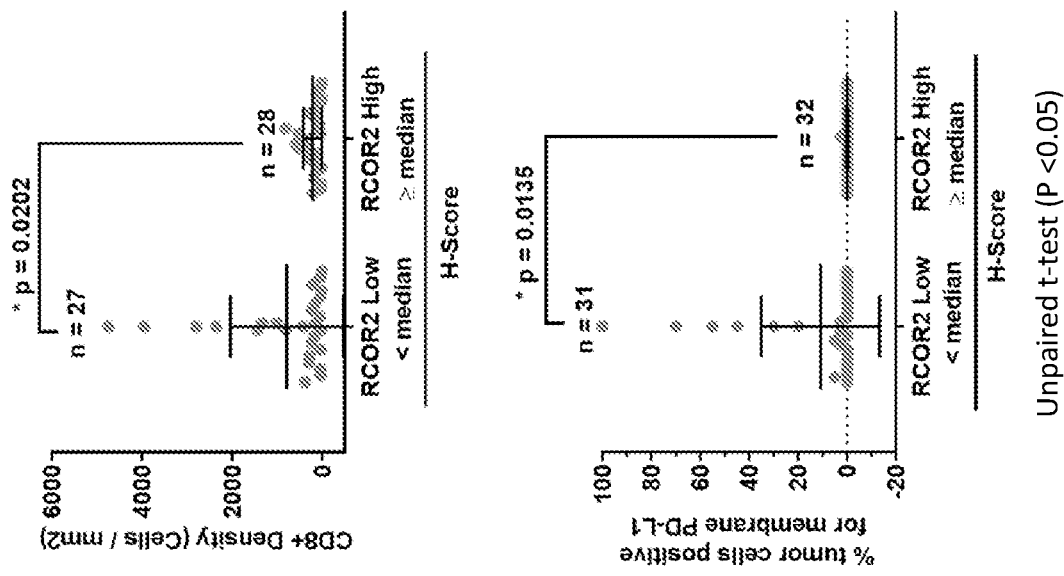
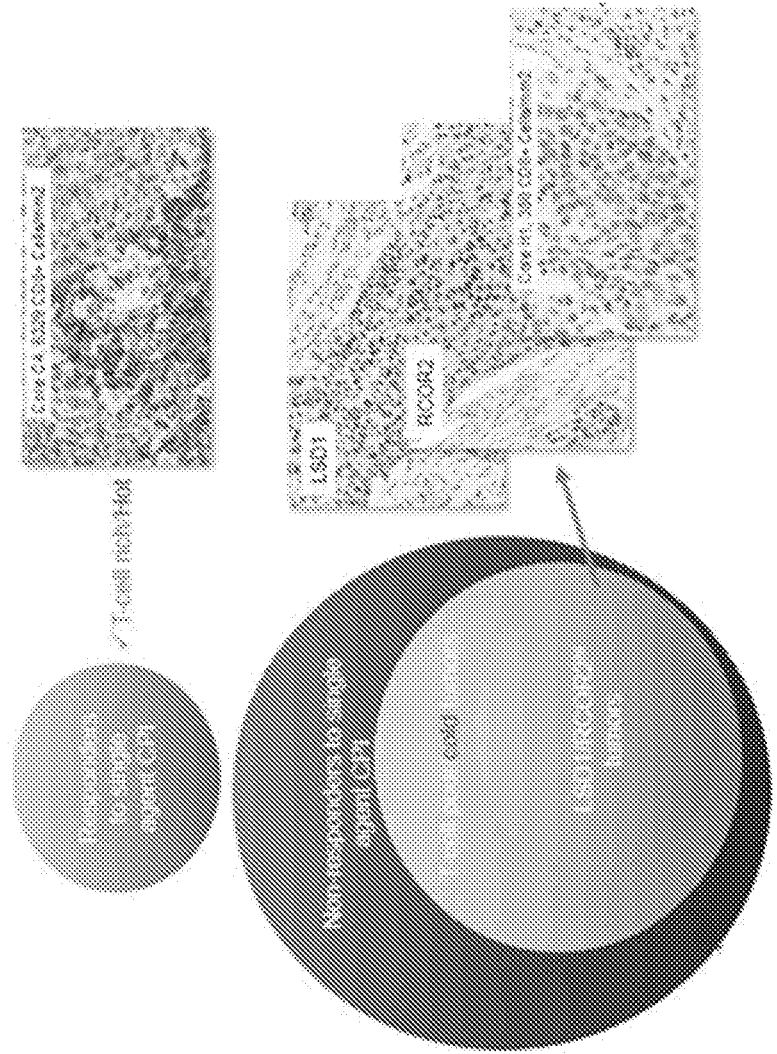
FIG. 2

FIG. 4

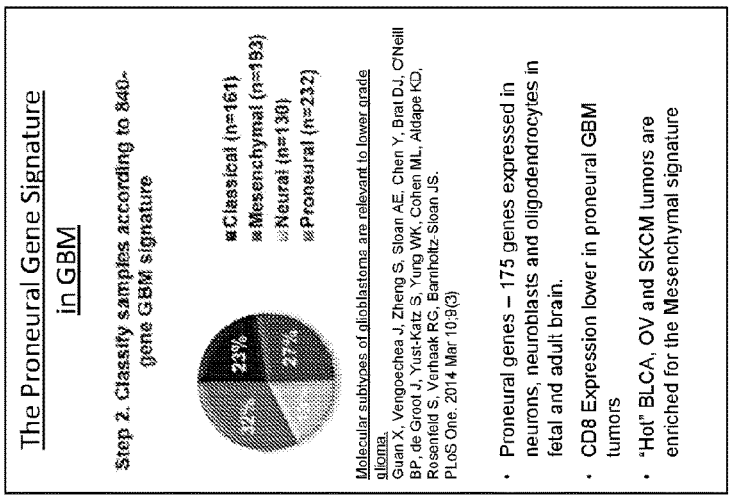

The Proneural Gene Signature in GBM

Step 2. Classify samples according to 840-gene GBM signature

- Classical (n=161)
- Mesenchymal (n=193)
- Neural (n=130)
- Proneural (n=232)

Molecular subtypes of glioblastoma are relevant to lower grade glioma.
Guan X, Vengoechea J, Zheng S, Sloan AE, Chen Y, Brat DJ, O'Neill BP, de Groot J, Yust-Katz S, Yung WK, Cohen ML, Aldape KD, Rosenfeld S, Verhaak RG, Barnholtz-Sloan JS.
PLoS One. 2014 Mar 10;9(3)

- Proneural genes – 175 genes expressed in neurons, neuroblasts and oligodendrocytes in fetal and adult brain.
- CD8 Expression lower in proneural GBM tumors
- "Hot" BLCA, OV and SKCM tumors are enriched for the Mesenchymal signature

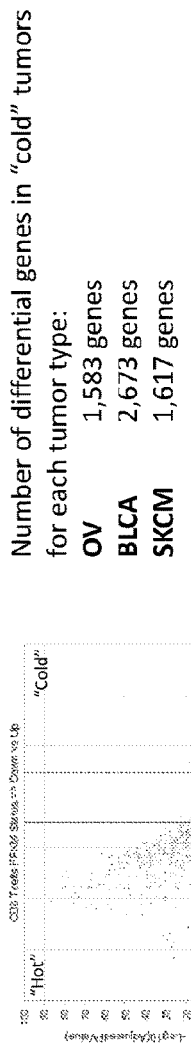

Number of differential genes in "cold" tumors for each tumor type:

| | |
|---|---|
| OV | 1,583 genes |
| BLCA | 2,673 genes |
| SKCM | 1,617 genes |

Gene set enrichment analysis identifies common biology (gene sets) in the cold tumor genes

| Ovarian (OV): | Bladder (BLCA): | Melanoma (SKCM): |
|---|---|---|
| GBM Proneural Signature | GBM Proneural Signature | GBM Proneural Signature |
| Neurogenesis Signature | Neurogenesis Signature | Neurogenesis Signature |
| Axonal guidance signaling | Axonal guidance signaling | Axonal guidance signaling |
| Hedgehog signaling | WNT Signaling | WNT Signaling |
| | Ephrin A Signaling | Ephrin A Signaling |

*Overlap: core 105 gene signature correlated with T cell exclusion shared across all three tumor types*

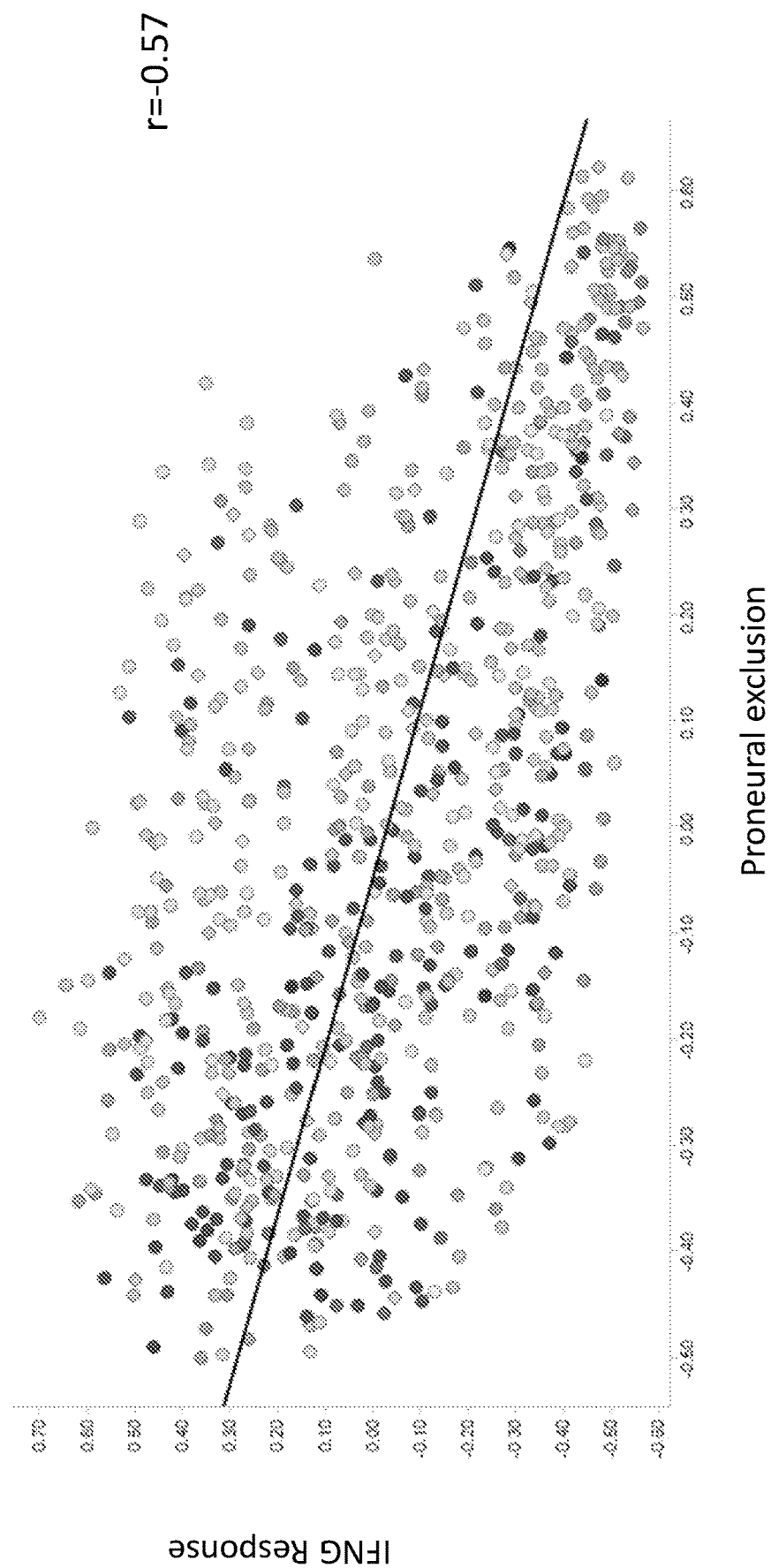

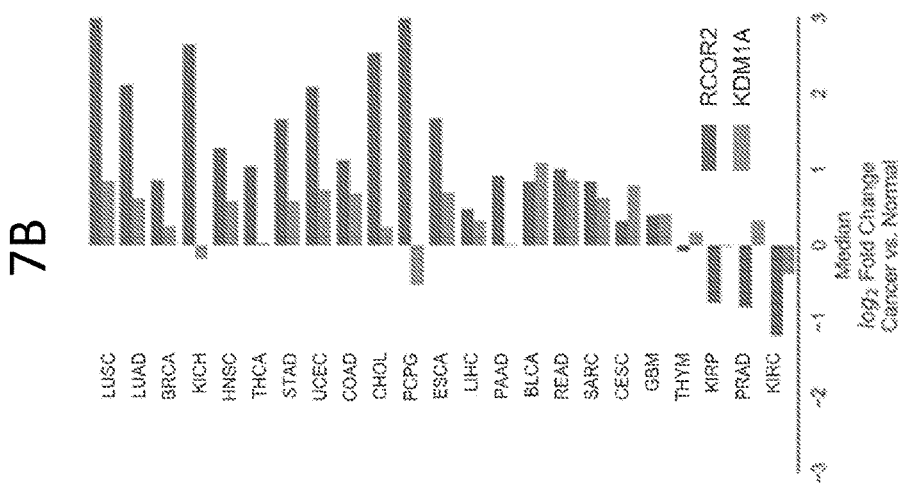
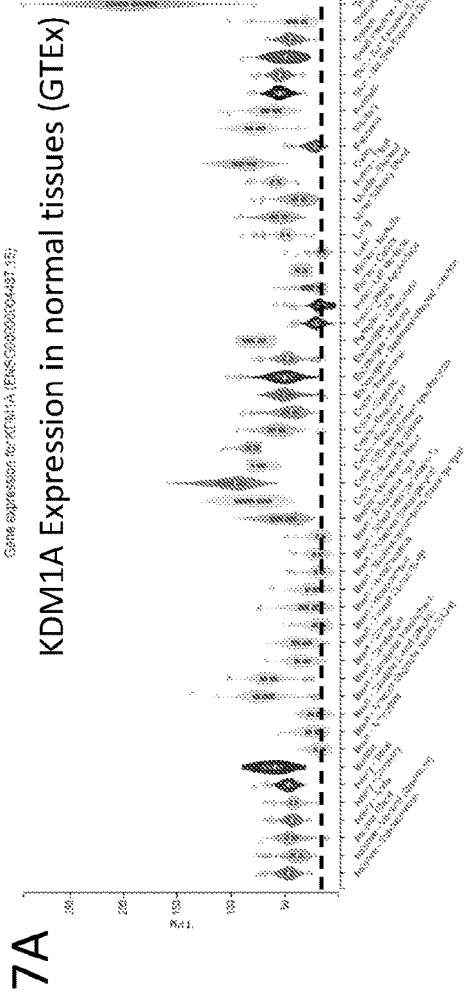
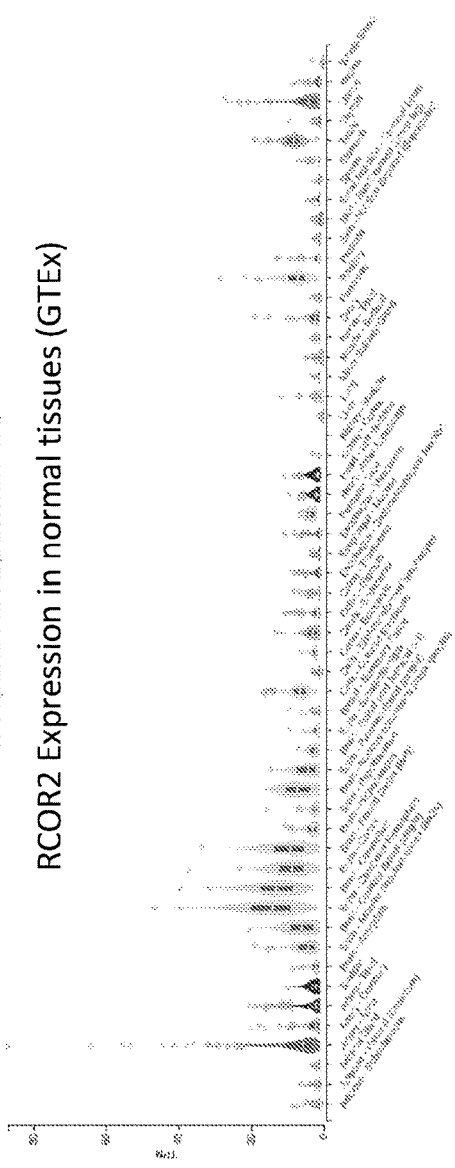
FIG. 7

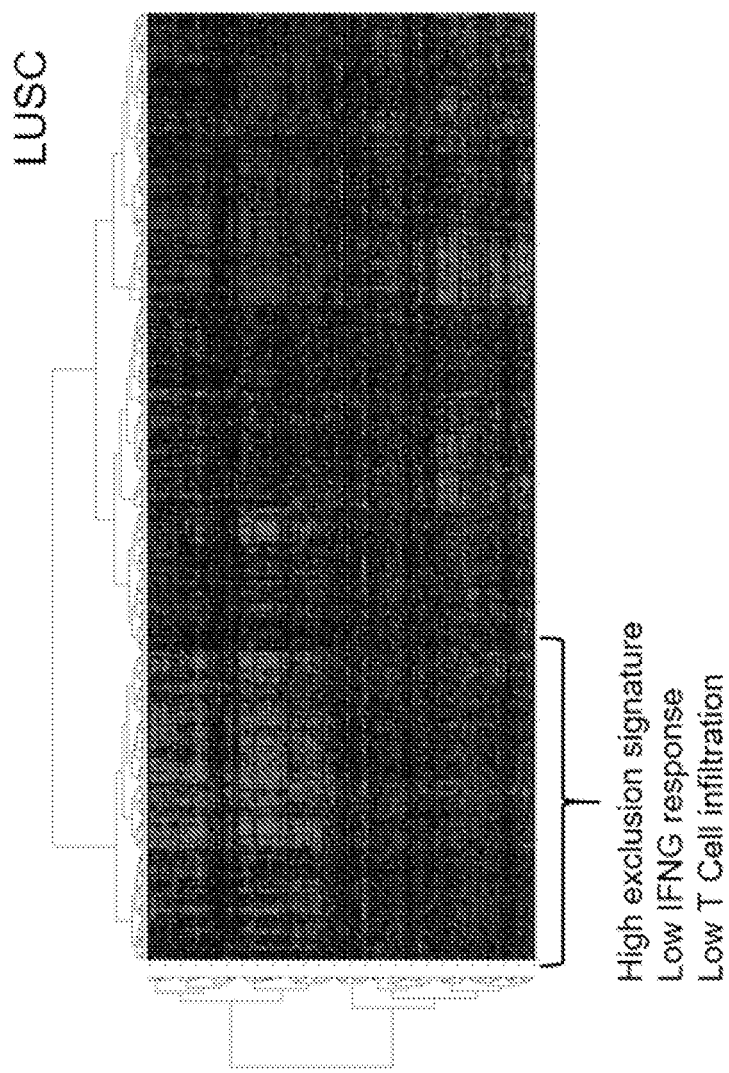

METHODS OF TREATING CANCER BY TARGETING COLD TUMORS

CROSS-REFERENCE TO RELATED APPLICATIONS

This application is the U.S. National Stage of International Patent Application No. PCT/US2020/037521, filed Jun. 12, 2020, which claims priority under 35 U.S.C. § 119 (e) to U.S. Provisional Patent Application No. 62/861,094, filed Jun. 13, 2019, the entire contents of these applications are incorporated herein by reference in their entirety.

FIELD

The embodiments described herein provide compositions, formulations, and methods for treating neoplastic diseases including both benign and malignant tumors, in which such treatments include therapies comprising administration of a lysine specific demethylase-1 (LSD-1) inhibitor. In some aspects, the administration of an LSD-1 inhibitor is for treating neoplastic diseases in certain patient populations comprising subjects with neoplastic cells that upregulate RE1 silencing transcription factor (REST) co-repressor 2 (RCOR2).

BACKGROUND

There remains a need for compositions, formulations, and methods for treating subjects with cancers such as, for example, basal cell carcinoma, relapsed or refractory non-Hodgkin's lymphomas (NHL), glioblastoma multiforme, anaplastic astrocytoma, or other advanced solid tumors.

While numerous cancer therapies have been identified over the past 20 years, not all cancers respond to current therapies. One promising cancer therapy relates to use of immune checkpoint inhibitors (CPIs). CPI therapy is a form of cancer immunotherapy. The therapy targets immune checkpoints. Immune checkpoints maintain immune homeostasis and prevent auto-immunity. Some cancers escape immune surveillance by activating immune checkpoint pathways to suppress antitumor immune responses. Checkpoint inhibitors work by releasing this "brake" in the immune system to promote the elimination of tumor cells. However, not all cancers respond to CPI therapy.

Despite remarkable clinical benefit of CPIs in many cancers, response rates are low (~10-30%). There remains a need in the art for new methods of treating neoplastic diseases, particularly for cancer patient populations who do not respond to current therapies. The present disclosure satisfies this need.

BRIEF SUMMARY OF THE INVENTION

In some aspects, the disclosure is drawn to methods of treating cancer in a subject in need thereof, the method comprising: (a) identifying a patient having a cancer tumor that is a diagnostic positive cold tumor; and (b) administering to the patient a composition comprising a therapeutically effective amount of a compound having the structure of Formula (I), or a pharmaceutically acceptable salt thereof,

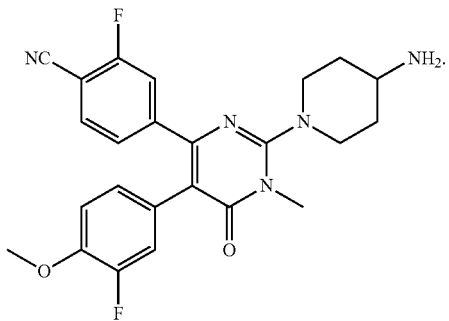 [SMILES: COc1ccc(-c2c(-c3ccc(C#N)c(F)c3)nc(N3CCC(N)CC3)n(C)c2=O)cc1F]

(I)

In some aspects, the patient (a) has failed single checkpoint inhibitor (CPI) therapy, has minimal response to CPI therapy, or no therapeutic effect is observed for CPI therapy; and (b) cells of the tumor display a high gene expression of REST Corepressor 2 RCOR2 relative to the median RCOR2 gene expression of tumors in other patients having the same tumor type.

In some aspects, the patient (a) is naïve to a CPI therapy; and (b) cells of the tumor display a high gene expression of RCOR2 relative to the median RCOR2 gene expression of tumors in other patients having the same tumor type. In some aspects, the high gene expression of RCOR2 is in the top 25% of expression of tumors in other patients having the same tumor type. In some aspects, the high gene expression of RCOR2 is in the top 10% of expression of tumors in other patients having the same tumor type.

In some aspects, (a) the CPI therapy comprises anti-programmed cell death protein 1 (PD1) and/or programmed death-ligand 1 (PD-L1) therapy; and (b) the patient's cancer cells display a high gene expression of RCOR2. In some aspects, (a) the patient's cancer exhibits a cold tumor signature; and (b) the patient's cancer cells display a high gene expression of RCOR2. In some aspects, the cold tumor signature is defined by: (a) low or no CD8 T cell infiltration within the tumor; (b) exhibition of T cell non-inflamed or T cell excluded based on the presence of T cells within the tumor. In some aspects, the presence of T cells within the tumor is measured or estimated by gene expression levels of T cell markers in bulk RNA profiling data.

In some aspects, the patient's cancer cells exhibit an increase in the gene expression of one or more of the following genes: AK056486, NKAIN1, FAM183A, SAMD13, LINC00622, CHRNB2, MEX3A, IGSF9, C1ORF192, CCDC181, OCLM, PPFIA4, PANK1, B4GALNT4, GAS2, MS4A8, MYRF, RCOR2, FLRT1, AK313893, NXPH4, BC073932, MSI1, CCDC169, FREM2, ATP7B, AF339817, AK124233, GPX2, PAR5, PLA2G4F, IGDCC3, GOLGA6L10, UBE2Q2P2, WDR93, PDIA2, CASKIN1, AK096982, TOX3, AK057689, C16ORF3, AK127378, EFNB3, DNAH2, ANKRD13B, SOCS7, RAMP2-AS1, FAM171A2, ADAM11, METAZO-A_SRP_75, CBX2, ZNF850, LOC100379224, TTYH1, VN1R1, MEIS1-AS3, LONRF2, BC022892, KLHL23, AX747067, CCDC108, IRS1, KIF1A, FLRT3, SIM2, IGSF5, CECR5-AS1, FAM227A, AX747137, FGD5P1, ACVR2B, LOC646903, FGFR3, FLJ13197, SLC10A4, TTC23L, MCIDAS, GUSBP9, GPR98, SEMA6A, PCDHGC4, USP49, TMEM151B, AK125212, PACRG, AK123300, COL28A1, SOSTDC1, AK098769, FKBP6, DPY19L2P4, EPO, CTTNBP2, KIAA1549, TAS2R5, FAM86B2, DQ595103, CHD7, AK094577, WNK2, TMEFF1, AL390170, MUM1L1, HS6ST2, and PNCK; wherein the increase in the gene expression is relative to the gene expression of a control gene.

In some aspects, the patient's cancer cells exhibit an increase in the gene expression of at least about 10% or at least about 15% of the genes where expression levels are measured. In some aspects, the patient's cancer cells exhibit an increase in the gene expression of at least about 20%, at least about 25%, at least about 30%, or at least about 35% of the genes where expression levels are measured. In some aspects, the patient's cancer cells exhibit an increase in the gene expression of at least about 40%, at least about 45%, at least about 50%, or at least about 55% of the genes where expression levels are measured. In some aspects, the patient's cancer cells exhibit an increase in the gene expression of at least about 60%, at least about 65%, at least about 70%, or at least about 75% of the genes where expression levels are measured. In some aspects, the patient's cancer cells exhibit an increase in the gene expression of at least about 80% of the genes where expression levels are measured.

In some aspects, the patient's cancer cells exhibit a decrease in the gene expression of one or more interferon response genes, wherein the decrease in the gene expression is relative to the gene expression of a control gene. In some aspects, the interferon response genes are selected from: AC124319.1, ADAR, APOL6, ARID5B, ARL4A, AUTS2, B2M, BANK1, BATF2, BPGM, BST2, BTG1, C1R, C1S, CASP1, CASP3, CASP4, CASP7, CASP8, CCL2, CCL5, CCL7, CD274, CD38, CD40, CD69, CD74, CD86, CDKN1A, CFB, CFH, CIITA, CMKLR1, CMPK2, CMTR1, CSF2RB, CXCL10, CXCL11, CXCL9, DDX58, DDX60, DHX58, EIF2AK2, EIF4E3, EPSTI1, FAS, FCGR1A, FGL2, FPR1, GBP4, GBP6, GCH1, GPR18, GZMA, HELZ2, HERC6, HIF1A, HLA-A, HLA-B, HLA-DMA, HLA-DQA1, HLA-DRB1, HLA-G, ICAM1, IDO1, IFI27, IFI30, IFI35, IFI44, IFI44L, IFIH1, IFIT1, IFIT2, IFIT3, IFITM2, IFITM3, IFNAR2, IFL10RA, IL15, IL15RA, IL18BP, IL2RB, IL4R, IL6, IL7, IRF1, IRF2, IRF4, IRF5, IRF7, IRF8, IRF9, ISG15, ISG20, ISOC1, ITGB7, JAK2, KLRK1, LAP3, LATS2, LCP2, LGALS3BP, LYSE, LYSMD2, 1-MAR, METTL7B, MT2A, MEHFD2, MVP, MX1, MX2, MYD88, NAMPT, NCOA3, NFKB1, NFKBIA, NLRC5, NMI, NOD1, NUP93, OAS2, OAS3, OASL, OGFR, P2RY14, PARP12, PARP14, PDE4B, PELI1, PFKP, PIM1, PLA2G4A, PLSCR1, PML, PNP, PNPT1, PSMA2, PSMA3, PSMB10, PSMB2, PSMB8, PSMB9, PSME1, PSME2, PTGS2, PTPN1, PTPN2, PTPN6, RAPGEF6, RBCK1, RIPK1, RIPK2, RNF31, RSAD2, RTP4, SAMD9L, SAMHD1, SECTM1, SELP, SERPING1, SLAMF7, SLC25A28, SOCS1, SOCS3, SOD2, SP110, SPPL2A, SRI, SSPN, ST3GAL5, ST8SIA4, STAT1, STAT2, STAT3, STAT4, TAP1, TAPBP, TDRD7, TNFAIP2, TNFAIP3, TNFAIP6, TNFAIP10, TOR1B, TRAFD1, TRIM14, TRIM 21, TRIM25, TRIM 26, TXNIP, UBE2L6, UPP1, USP18, VAMP5, VAMP8, VCAM1, WARS, XAF1, XCL1, ZBP1, and ZNFX1.

In some aspects, the patient's cancer cells exhibit a decrease in the gene expression of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the interferon response genes where expression levels are measured.

In some aspects, (a) the compound of Formula (I) or a pharmaceutically acceptable salt thereof is an inhibitor of Lysine-specific histone demethylase 1 (LSD-1); and/or (b) the compound of Formula (I) or a pharmaceutically acceptable salt thereof is a reversible antagonist to LSD-1; and/or (c) the compound of Formula (I) or a pharmaceutically acceptable salt thereof is a reversible inhibitor of LSD-1.

In some aspects, when LSD-1 is blocked, infiltration of T cells is thereby enabled, thus allowing anti-PDL1 and/or anti-PD1 therapy to block T-cell inhibition and thus retard tumor growth and/or reduce tumor size. In some aspects, LSD-1 is inhibited from demethylating histone complexes, and thereby infiltration of T cells is enabled, thus allowing anti-PDL1 and/or anti-PD1 therapy to retard tumor growth and/or tumor size. In some aspects, LSD-1 is prevented from forming a functional protein complex with RCOR2, and thereby infiltration of T cells is enabled, thus allowing anti-PDL1 and/or anti-PD1 therapy to retard tumor growth and/or tumor size.

In some aspects, the subject's cancer has a high non-synonymous mutational burden. In some aspects, (a) the patient is concurrently treated with a therapeutically effective amount of at least one CPI therapy, which can be an anti-PDL1 and/or anti-PD1 therapy; and/or (b) the patient is treated sequentially with the composition comprising the compound of Formula (I) or a pharmaceutically acceptable salt thereof, and at least one CPI therapy, which can be an anti-PDL1 and/or anti-PD1 therapy; and/or (c) the composition comprising the compound of Formula (I) or a pharmaceutically acceptable salt thereof, additionally comprises at least one CPI therapy, which can be an anti-PDL1 and/or anti-PD1 therapy.

In some aspects, the combination of treatment with a composition comprises (i) a therapeutically effective amount of the compound of Formula (I) or a pharmaceutically acceptable salt thereof, and (ii) at least one CPI therapy, which can be an anti-PDL1 and/or anti-PD1 therapy, results in an increase in survival of the patient and/or a slowing of tumor growth, as compared to administration of the composition comprising the compound of Formula (I) or a pharmaceutically acceptable salt thereof alone or the CPI therapy alone.

In some aspects, tumor growth is slowed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by any clinically recognized method. In some aspects, the patient's survival is increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as compared to mean survival times exhibited with patients administered the composition alone and/or the anti-PDL1 and/or anti-PD1 therapy alone.

In some aspects, the CPI therapy is an anti-PD1 therapy selected from the group consisting of: (a) nivolumab; (b) pembrolizumab; (c) cemiplimab; (d) spartalizumab; (e) camrelizumab; (f) sintilimab; (g) tislelizumab; (h) toripalimab; (i) AMP-224; (j) MEDI0680; (k) durvalumab; and (1) tislelizumab. In some aspects, the CPI therapy is an anti-PDL1 therapy selected from the group consisting of: (a) atezolizumab; (b) avelumab; (c) durvalumab; (d) KN035; (e) CK-301; (f) CA-170; and (g) BMS-986189.

In some aspects, the composition further comprises a therapeutically effective amount of etoposide; or (b) an additional composition comprising a therapeutically effective amount of etoposide is administered. In some aspects, (a) the composition further comprises a therapeutically effective amount of a platin, and optionally the platin can be selected from the group consisting of cisplatin, carboplatin, exaliplatin, nedaplatin, triplatin tetranitrate, phenanthriplantin, picoplatin, and satraplatin; or (b) an additional composition comprising a therapeutically effective amount of a platin is administered, and optionally wherein the platin is selected from the group consisting of cisplatin, carboplatin, exaliplatin, nedaplatin, triplatin tetranitrate, phenanthriplantin, picoplatin, and satraplatin.

In some aspects, the patient has a cancer selected from the group consisting of lung cancer, small cell lung cancer (SCLC), lung squamous cell carcinoma (LUSC), head and neck squamous cell carcinoma (HNSC), HPV-negative head and neck squamous cell carcinoma (HNSC HPV neg), bladder carcinoma (BLCA), bladder urothelial carcinoma, melanoma, skin cutaneous melanoma (SKCM), breast cancer, triple negative breast cancer (TNBC), ovarian cancer (OV), stomach cancer, stomach adenocarcinoma (STAD), sarcomas (SARC), glioma, neuroendocrine tumors, advanced solid tumors, prostate cancer, marginal zone lymphoma, pancreatic cancer, pancreatic adenocarcinoma (PAAD), pancreatic ductal adenocarcinoma (PDAC), pancreatic neuroendocrine tumors (PNET), low grade glioma (LGG), cervical squamous cell carcinoma and endocervical adenocarcinoma (CESC), testicular germ cell tumors (TGCT), kidney renal clear cell carcinoma (KIRC), kidney renal papillary cell carcinoma (KIRP), and esophageal carcinoma (ESCA).

In some aspects, the patient has a cancer selected from the group consisting of melanoma, metastatic non-small cell lung cancer, head and neck squamous cell carcinoma, squamous cell lung cancer, renal cell carcinoma, Hodgkin's lymphoma, cutaneous squamous cell carcinoma (CSCC), patients with locally advanced CSCC who are not candidates for curative surgery or curative radiation, solid tumors and lymphomas, relapsed or refractory classical Hodgkin lymphoma, small cell lung cancer (SCLC), solid tumors and hematologic cancers.

In some aspects, the composition comprising the compound of Formula (I) or a pharmaceutically acceptable salt thereof is administered at least once weekly. In some aspects, the composition comprising the compound of Formula (I) or a pharmaceutically acceptable salt thereof, is administered daily, every other day, every 3 days, every 4 days, every 5 days, once weekly, twice weekly, three times weekly, every other week, or any other suitable dosing period. In some aspects, the compound of Formula (I) or a pharmaceutically acceptable salt thereof, is in the form of an injectable solution.

In some aspects, the compound of Formula (I) or a pharmaceutically acceptable salt thereof is administered as an intravenous injection. In some aspects, the compound of Formula (I) or a pharmaceutically acceptable salt thereof, is adapted for oral administration.

The foregoing general description and following description of the drawings and detailed description are exemplary and explanatory and are intended to provide further explanation of the subject matter as claimed. Other objects, advantages, and novel features will be readily apparent to those skilled in the art from the following brief description of the drawings and detailed description of the invention.

DESCRIPTION OF THE DRAWINGS

FIG. 2 visually maps out preferred patient populations to be treated with methods described herein, with "CPI" representing an immune checkpoint inhibitor. Based on immunohistochemistry (IHC) results from small cell lung cancer (SCLC) tumors, the diagram shows that patient populations have high expression of the gene RCOR2, which is a subset of those with low abundance of T-cells, which is a subset of those which do not respond well to CPIs.

FIG. 3 graphically shows the preferred patient population as having high expression of RCOR2 or high proneural score on the x-axis, low T cell infiltration and non-responsive to single CPI treatment on the y-axis.

FIG. 4 shows the results of a gene set enrichment analysis identifying common biology (gene sets) in the cold tumor genes, with the number of differential genes in "cold" tumors for each tumor type being Ovarian (1,583 genes), bladder cancer (2,673 genes), and melanoma (1,617 genes). OV (Ovarian)=GBM Proneural Signature, Neurogenesis Signature, Axonal guidance signaling, and Hedgehog signaling. BLCA (Bladder cancer)=GBM Proneural Signature, Neurogenesis Signature, Axonal guidance signaling, WNT Signaling, and Ephrin A Signaling. SKCM (Melanoma)=GBM Proneural Signature, Neurogenesis Signature, Axonal guidance signaling, WNT Signaling, and Ephrin A Signaling. Overlap=core 105 proneural gene signature anti-correlated with T cell infiltration and interferon response genes shared across all three tumor types.

FIG. 6B shows a graph of proneural exclusion vs. IFNG response in the CCLE dataset of cell lines.

FIGS. 7A and 7B depict expression of RCOR2 (blue in FIG. 7B) and KDM1A, also known as LSD-1 (orange in FIG. 7B) in normal and tumor tissues. RCOR2 is expressed at low levels in most normal tissues (FIG. 7A) and is highly upregulated in cancer (FIG. 7B). In contrast, LSD1 is more highly expressed in normal tissues (FIG. 7A) and is modestly upregulated in cancer relative to normal tissue (FIG. 7B) as compared to RCOR2.

FIG. 8 shows a heatmap demonstrating that approximately one third of LUSC samples have high expression of proneural signature genes (referred to as "high exclusion signature") and low expression of IFNG response genes and genes expressed by T cells. Each row is a gene and each column is a LUSC sample. The color shows the relative expression of that gene in a sample. High expression (Red) vs Low expression (green).

DETAILED DESCRIPTION OF THE INVENTION

I. Overview

Figure 1:
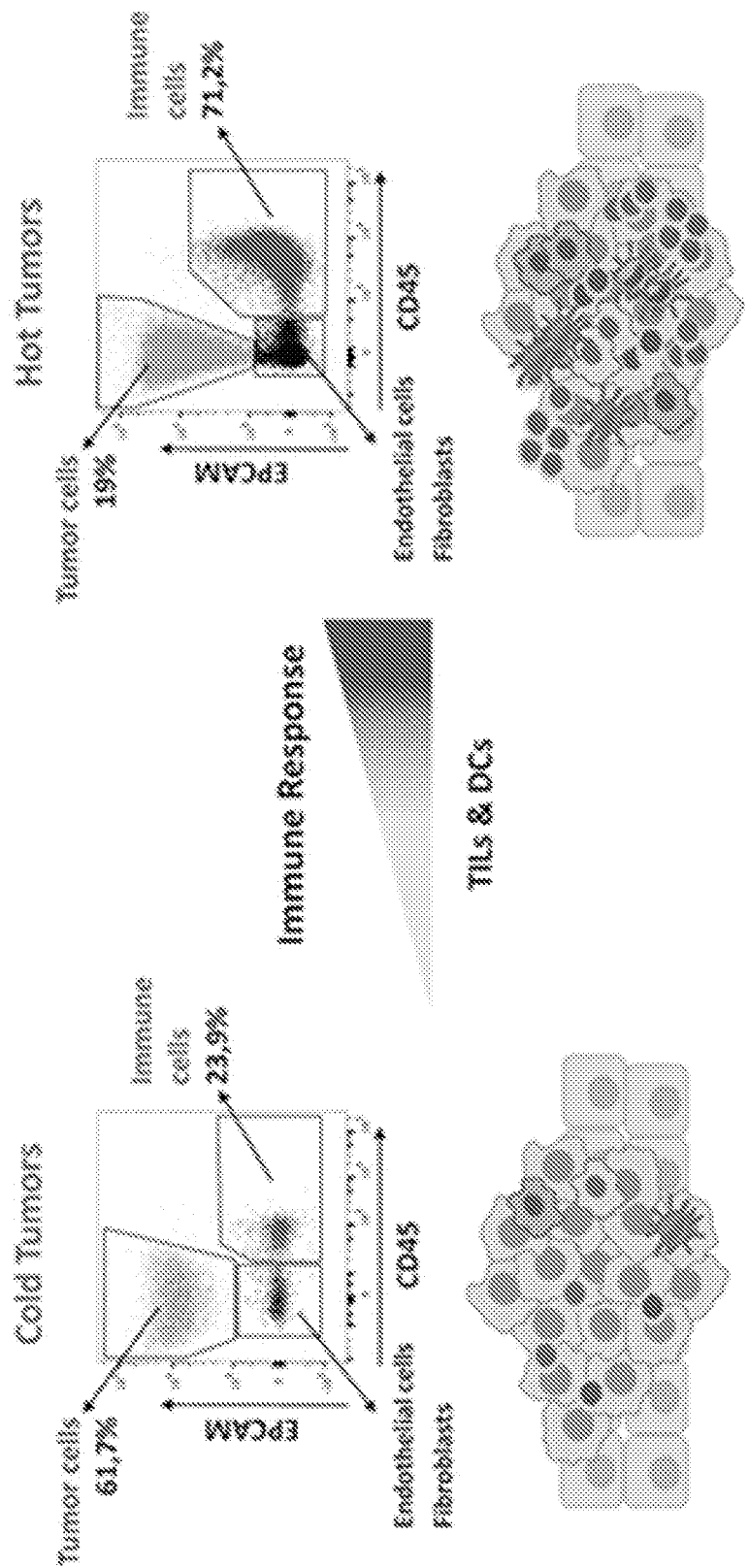
FIG. 1 is a comparison of characteristics of "cold" versus "hot" tumors, reproduced from Ramos et al., "Mechanisms of Resistance to Immune Checkpoint Antibodies." *Handb. Exp. Pharmacol.* (Mar. 18, 2017).

The emergence of CPI therapies over the last decade has transformed cancer treatment in a wide range of tumor types. Unprecedented and durable clinical responses in difficult-to-treat cancer histologies have been observed. However, despite these promising long-term responses, the majority of patients fail to respond to immune checkpoint blockade, demonstrating primary resistance. Additionally, many patients who initially respond to treatment eventually experience relapse secondary to acquired resistance. Both primary and acquired resistance are a result of complex and constantly evolving interactions between cancer cells and the immune system.

The ability for tumors to induce adaptive immune responses relies on recognition of cancer cells as foreign. High tumor mutational burden (TMB), with accompanying elevated neoantigen expression, plays an important role in antitumor immunity. The response rates of different tumor types to PD-1/PD-L1 checkpoint inhibitors tend to be proportional to their corresponding TMB. However, tumors with similar TMB can have very different responses to CPIs, indicating that response to the immune checkpoint blockade is complex, heterogeneous, and inconsistent and that additional mechanisms are at play. Increased PD-L1 expression has been correlated with immune response and is used as a biomarker for CPI therapy in small cell lung cancer and urothelial carcinoma. Additionally, elevated numbers of tumor-infiltrating lymphocytes have been noted in responsive cancers. See Fares et al., *American Society of Clinical Oncology Educational Book,* 39:147-164 (2019).

One of the greatest challenges for the field of cancer immunotherapy is understanding the complex resistance mechanisms and to develop effective combination strategies to overcome resistance. According to the time of occurrence, resistance can be primary, as in a patient never responds, or acquired, which emerges after a period of response. In addition, resistance can also be classified as intrinsic or extrinsic to tumor cells. Intrinsic resistance is seen when cancer cells alter processes that are related to immune recognition, cell signaling, gene expression, and DNA damage response. Extrinsic resistance occurs external to tumor cells throughout the T-cell activation process.

Over time some tumor types become resistant to PD1/PD-L1 checkpoint inhibitor therapy. The compounds described herein, inhibit LSD1, and thus increase tumor responsiveness to anti-PD1 agents. LSD1 is in a functional complex with RCOR2. Accordingly, RCOR2 expression is expected to be an indicator of tumors which have active LSD1 and will respond to the compounds described herein, particularly when they are given in combination with a CPI.

The present disclosure describes the discovery of multiple indicia for identifying patients and patient populations that exhibit a type of tumor—referred to as "cold" tumors—that are sensitive to the compounds and formulations described herein, including tumors that have become resistant to CPIs.

Tumors can be categorized as "hot" (immune cell infiltration or inflamed) or "cold" (immune cell infiltration exclusion or immune desert). Immune cell (e.g. T cells) infiltration into tumors is prognostic for many tumor types, a predictor for response to checkpoint blockade therapy, and required for adoptive T cell therapies to be effective. Other immune cell types generally correlate with the presence of T cells in the tumor. The abundance of T cells in tumors can be estimated by gene expression of T cell marks in bulk RNA data. Hot tumors are associated with an abundance of immune cells including T cells, while cold tumors are associated with a dearth of immune cells including T cells. See Ramos et al., *Handb. Exp. Pharmacol.,* 249:109-128 (2017) and FIG. 1.

As detailed herein, multiple indicators for identifying "cold" tumors have been identified, including for example low interferon response gene signature, low tumor immune infiltrate, high proneural exclusion gene signature, and/or high RCOR2 expression. In some aspects, the "low" or "high" refers to a contrast between appropriate experimental or clinical control(s). Furthermore, treatment of tumors that are diagnostic positive as "cold" tumors with compounds described herein (compound of Formula (I) and its besylate salt) is expected to enhance immune cell (e.g. T cells) infiltration in these tumors, which is expected to be particularly beneficial for subjects having "cold" tumors, and therefore in need of enhancement of T-cell infiltration.

In one aspect of the methods described herein, one or more of the cancer patient populations described herein are expected to respond particularly well to treatment with the compound of Formula (I) or a pharmaceutically acceptable salt thereof, such as a besylate salt thereof.

In some aspects, the treatment is combined with one or more CPIs, wherein the cancer patient population is defined as one where a subject (i) is not expected to respond to a CPI (ii) has failed CPI therapy (e.g., anti-PD1, anti-PD1, and/or anti-PDL1 no longer works), and/or (iii) displays a high RCOR2 gene expression profile. In some aspects, the treatment is combined with one or more CPIs, wherein the cancer patient population is defined as one where a subject (i) is not expected to respond to a CPI (ii) has failed CPI therapy (e.g., anti-PD1, anti-PD1, and/or anti-PDL1 no longer works), and (iii) displays a high RCOR2 gene expression profile. In some aspects, the treatment is combined with one or more CPIs, wherein the cancer patient population is defined as one where a subject (i) is CPI naïve, (ii) displays a high RCOR2 gene expression profile, and (iii) has low or no detectable T cell infiltration (cold tumor).

In some aspects, the cancer patient populations are identified as those that comprise one or more cancer tumors that are diagnostic positive for (1) low interferon response gene signature, (2) low immune cell infiltrate, (3) high RCOR2 gene expression, and/or (4) high proneural signature.

In some aspects, one or more of the cancer patient populations described herein are expected to respond favorably to treatment with compounds described herein, particularly when the compounds are given in combination with a CPI.

II. Compound of Formula (I)

In some aspects, the disclosure is generally drawn to a method of treating cancer in a subject in need thereof, comprising: (a) identifying a cancer patient having "cold" tumor cells as described herein; and (b) administering to the patient a composition comprising a therapeutically effective amount of an LSD1 inhibitor compound having the structure of Formula (I), or a pharmaceutically acceptable salt thereof, such as a besylate salt,

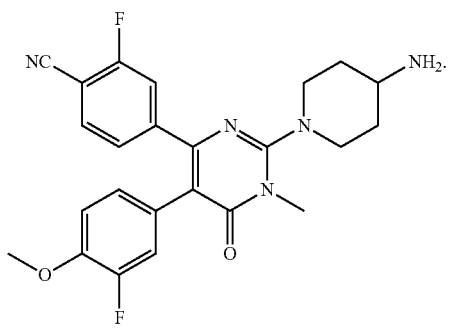 [SMILES: COc1ccc(-c2c(-c3ccc(C#N)c(F)c3)nc(N3CCC(N)CC3)n(C)c2=O)cc1F]

(I)

The chemical name of the above compound is 4-[2-(4-Amino-piperidin-1-yl)-5-(3-fluoro-4-methoxy-phenyl)-6-oxo-1,6-dihydro-pyrimidin-4-yl]-2-fluoro-benzonitrile, with a chemical formula of $C_{23}H_{21}F_2N_5O_2$, molecular weight of 437.44, and CAS number of 1821307-10-1. 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile is described in U.S. Pat. No. 9,255,097.

In another aspect, the LSD1 inhibitor is a benzenesulfonic acid salt (also known as besylate salt) of the compound of Formula (I).

Methods are provided herein for the treatment of relapsed and/or refractory solid tumors (including neuroendocrine carcinomas (NEC)) and non-Hodgkin's lymphomas (NHLs) and the like, using the compound of Formula (I) or a pharmaceutically acceptable salt thereof, such as a besylate salt thereof, and pharmaceutical compositions comprising compounds useful for the inhibition of lysine specific demethylase-1 (LSD-1). In one aspect, preferred cancer patient populations, described herein, are treated with the methods described herein.

The compound of Formula (I) is described in U.S. Pat. No. 9,255,097, U.S. application Ser. No. 14/988,022, filed Jan. 5, 2016, U.S. application Ser. No. 15/018,814, filed Feb. 8, 2016, and International patent application No. PCT/US2015/028635, all of which claim the priority benefit of U.S. Application No. 61/987,354, filed May 1, 2014; as well as those described in U.S. Application No. 62/251,507, filed Nov. 5, 2015. Background regarding compounds used in the methods described herein is described in U.S. Pat. Nos. 9,255,097 and 10,328,077. The contents of each and every one of these applications are specifically incorporated by reference in their entireties for all purposes.

In some embodiments, the compounds disclosed herein are capable of inhibiting LSD-1 activity in a biological sample by contacting the biological sample with the compound of Formula (I) or a pharmaceutically acceptable salt thereof, such as a besylate salt thereof. In some embodiments, the compound of Formula (I) or a pharmaceutically acceptable salt thereof, such as a besylate salt thereof, is capable of modulating the level of histone-4 lysine-3 methylation in the biological sample. In some embodiments, the compound of Formula (I) or a pharmaceutically acceptable salt thereof, such as a besylate salt thereof, is capable of modulating histone-3 lysine-9 methylation levels in the biological sample.

In particular, it is believed that the compounds described herein increase response to anti-PD1 agents by inhibiting LSD1. LSD1 is in a functional complex with RCOR2. Accordingly, high RCOR2 expression is expected to be an indicator of tumors which have active LSD1 and will respond to the compounds described herein, particularly when they are given in combination with a CPI.

LSD1 has a fair degree of structural similarity and amino acid identity/homology to polyamine oxidases and monoamine oxidases, all of which (i.e., MAO-A, MAO-B and LSD-1) are flavin dependent amine oxidases which catalyze the oxidation of nitrogen-hydrogen bonds and/or nitrogen-carbon bonds. LSD1 also includes an N-terminal SWRIM domain. There are two transcript variants of LSD1 produced by alternative splicing.

The compound of Formula (I) or a pharmaceutically acceptable salt thereof, such as a besylate salt thereof, lack significant MAO-A or MAO-B inhibitory activity. In some embodiments, the compound of Formula (I) or a pharmaceutically acceptable salt thereof, such as a besylate salt thereof, inhibits LSD1 inhibitory activity to a greater extent than MAO-A and/or MAO-B inhibitory activity.

While not intended to be bound by any theory, it is not believed that the compounds described herein block expression of LSD1.

III. Immune Checkpoint Inhibitors

Immune checkpoints refer to a plethora of inhibitory pathways hardwired into the immune system, which, under normal physiological conditions are crucial for maintaining self-tolerance and modulating the duration and amplitude of physiological immune responses in peripheral tissues to minimize collateral tissue damage in response to pathogenic infection. However, the expression of immune checkpoint proteins is often dysregulated by tumors as an important immune resistance and escape mechanism.

Because many of the immune checkpoints are initiated by ligand-receptor interactions, they can be readily blocked by antibodies or modulated by recombinant forms of ligands or receptors. Thus, inhibition of these pathways appears to be a promising approach to activating therapeutic antitumor immunity. For example, Cytotoxic T-lymphocyte-associated antigen 4 (CTLA4) antibodies were the first of this class of immunotherapeutics to achieve US Food and Drug Administration (FDA) approval. Preliminary clinical findings with inhibitors of additional immune-checkpoint proteins, such as programmed cell death protein 1 (PD1), indicate broad and diverse opportunities to enhance antitumor immunity with the potential to produce durable clinical responses.

T cell activation through blockade of immune checkpoints has been a major focus of efforts to therapeutically manipulate endogenous antitumor immunity, owing to the capacity of T cells for the selective recognition of peptides derived from proteins in all cellular compartments; their capacity to directly recognize and kill antigen-expressing cells (by CD8+ effector T cells; also known as cytotoxic T lymphocytes (CTLs)); and their ability to orchestrate diverse immune responses (by CD4+ helper T cells), which integrate adaptive and innate effector mechanisms. Thus, agonists of co-stimulatory receptors or antagonists of inhibitory signals, both of which result in the amplification of antigen-specific T cell responses, are currently agents of interest in clinical testing.

TABLE 1

Table 1. Non-limiting list of immune checkpoint targets. Exemplary CPIs include, but are not limited to, anti-PDL1 and/or anti-PD1.

| Target | Biological Function |
| --- | --- |
| CTLA4 | Inhibitory Receptor |
| PD1 | Inhibitory Receptor |
| PDL1 | Ligand for PD1 |
| LAG3 | Inhibitory Receptor |
| B7.1 | Costimulatory Molecule |
| B7-H3 | Inhibitory Ligand |
| B7-H4 | Inhibitory Ligand |
| TIM3 | Inhibitory Receptor |
| VISTA | Inhibitory Receptor |
| CD137 | Costimulatory Molecule |
| OX-40 | Costimulatory Receptor |
| CD40 | Costimulatory Molecule |
| CD27 | Costimulatory Receptor |
| CCR4 | Costimulatory Receptor |
| GITR | Costimulatory Receptor |
| NKG2D | Activating Receptor |
| KIR | Costimulatory Receptor |

CTLA4, cytotoxic T-lymphocyte-associated antigen 4; LAG3, lymphocyte activation gene 3; PD1, programmed cell death protein 1; PDL, PD1 ligand; TIM3, T cell membrane protein 3; VISTA, V-domain immunoglobulin (Ig)-containing suppressor of T-cell activation; KIR, killer IgG-like receptor.

Current immune CPIs approved or in development include, but are not limited to, YERVOY® (ipilimumab), OPDIVO™ (nivolumab), KEYTRUDA® (pembrolizumab), tremelimumab, galiximab, MDX-1106, BMS-936558, MEDI4736, MPDL3280A, MEDI6469, BMS-986016, BMS-663513, PF-05082566, IPH2101, KW-0761, CDX-1127, CP-870, CP-893, GSK2831781, MSB0010718C, MK3475, CT-011, AMP-224, MDX-1105, IMP321, and MGA271, as well as numerous other antibodies and/or fusion proteins directed to the immune checkpoint proteins noted in Table 1. Common immune checkpoint proteins that may be targeted by checkpoint inhibitors (CPIs) include, but are not limited to B7.1, B7-H3, LAG3, CD137, KIR, CCR4, CD27, OX40, GITR, CD40, CTLA4, PD-1, and PD-L1.

In some aspects, the CPI therapy is selected from one or more of anti-PD-1, anti-PDL1, anti-CTLA4, anti-LAG3, anti-B7.1, anti-B7H3, anti-B7H4, anti-TIM3, anti-VISTA, anti-CD137, anti-OX40, anti-CD40, anti-CD27, anti-CCR4, anti-GITR, anti-NKG2D, and anti-KIR.

IV. Indicia of "Cold" Tumors

In some aspects, preferred cancer patient populations are identified as those that comprise one or more "cold" cancer tumors that are diagnostic positive for (1) low interferon signature, (2) low immune cell infiltrate, (3) high RCOR2 expression, and/or (4) high proneural signature. In some aspects, preferred cancer patient populations are identified as those that comprise one or more "cold" cancer tumors that are diagnostic positive for high RCOR2 expression and/or high proneural signature. In some aspects, preferred cancer patient populations are identified as those with cancers that exhibit high expression of RCOR2. In some aspects, preferred cancer patient populations are identified as those with cancers that exhibit high proneural signature. In some aspects, preferred cancer patient populations are identified as those with cancers that exhibit high expression of RCOR2 and high proneural signature.

In some aspects, preferred cancer patient populations are identified as those that diagnostic positive for high gene expression of RCOR2 relative to the average RCOR2 gene expression of tumors in other patients having the same tumor type. In some aspects, preferred cancer patient populations are identified as those that diagnostic positive for high gene expression of RCOR2 relative to the median RCOR2 gene expression of tumors in other patients having the same tumor type. In some aspects, high gene expression of RCOR2 is in the top 5%, 10%, 15%, 20%, 25%, 30%, 35%, 40%, 45%, 50%, 55%, 60%, 65%, 70%, 75%, 80%, 90%, or 95% of expression of tumors in other patients having the same tumor type. In some aspects, high gene expression of RCOR2 is in the top 50% of expression of tumors in other patients having the same tumor type.

Figure 3:
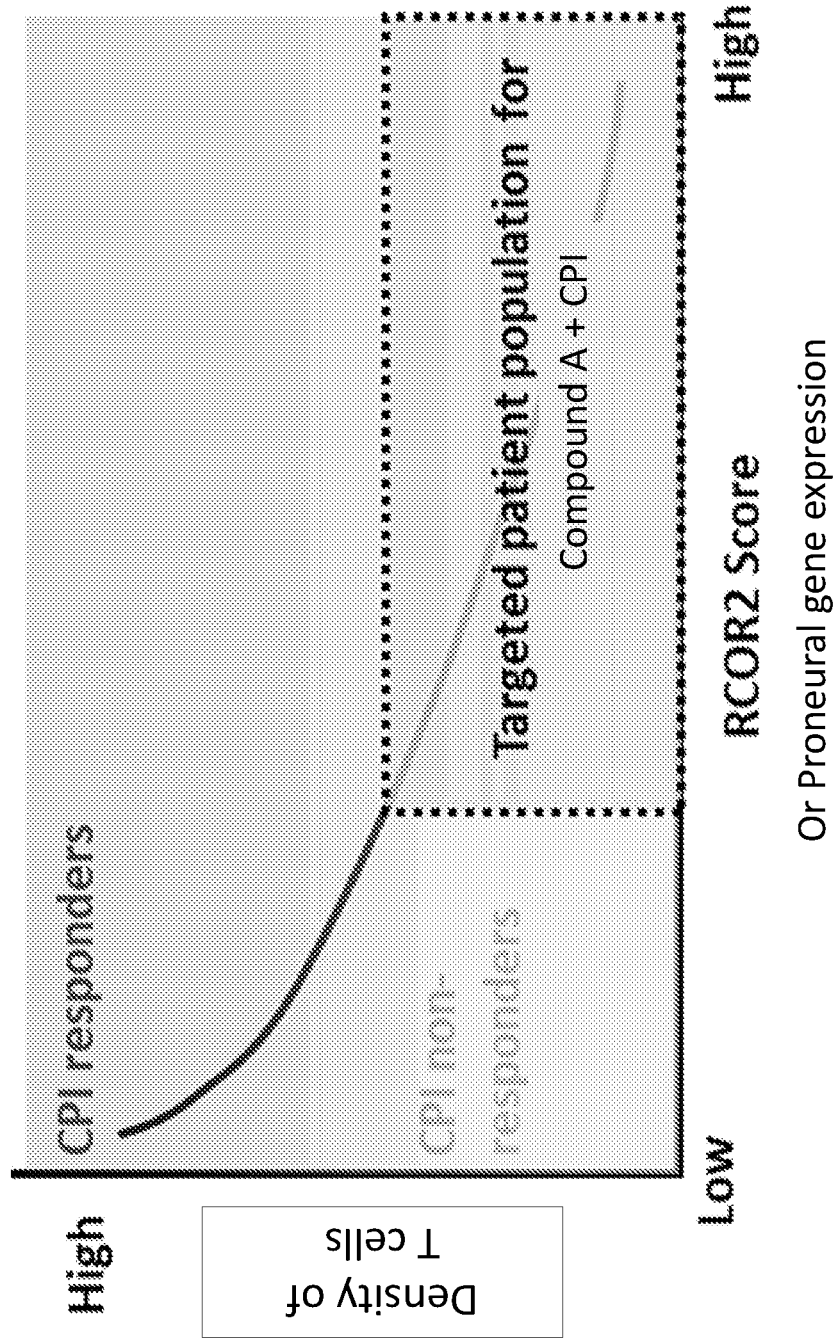
FIG. 3 visually maps out preferred patient populations to be treated with methods described herein.

In some aspects, FIGS. 2 and 3 visually map out preferred patient populations to be treated with methods described herein. FIG. 2 shows that patient populations having "hot" tumors, which are T cell rich, respond to single agent CPI treatment. However, patient populations having "cold" tumors, which have low/no T cell infiltration, do not respond to treatment with a single agent CPI. Patients having cancer cells with high expression of RCOR2 can benefit from treatment with an LSD1 inhibitor, the compound of Formula (I) or a pharmaceutically acceptable salt thereof, such as a besylate salt thereof. This is because the LSD1 inhibitor is a reversible antagonists of LSD1, which is expected to allow for the infiltration of T cells, and thus enhance activity of a CPI, such as anti-PD1 compound to act against the cancer cells. Similarly, FIG. 3 graphically shows the preferred patient population as having high expression of RCOR2 signature and thus low T cell infiltration, and non-responsiveness to single CPI treatment.

As described in the examples below, TCGA RNA-Seq data was used to identify genes associated with T Cell Exclusion (TCE) ("Cold" tumors). Tumor types with a range of hot and cold tumor samples, varying response rates to IO therapy, and a high number of patients in the data set were utilized—Ovarian (OV, n=430); Bladder (BLCA, n=411); and Melanoma (SKCM, n=368). Within each tumor type, samples were ranked by the expression of the single gene CD8A, and divided into quartiles with $1^{st}$ (lowest expression) being labelled cold and $4^{th}$ (highest expression) being labeled hot. See FIG. 4 (showing overlap of gene expression in 3 tumor types; a core 105 proneural gene signature correlated with T cell exclusion was found to be shared across all three tumor types.

Differential gene expression analysis between the $1^{st}$ and $4^{th}$ quartiles of samples identified two sets of genes for each tumor type. Hot genes—e.g., genes with significantly higher expression in hot samples (High CD8A) and Cold genes—e.g., genes with significantly higher expression in cold samples (low CD8A). Pathway and gene signature analysis was performed for each gene list, and there was a 105 proneural T cell exclusion gene signature shared across multiple tumor types. Thus, across all three tumor types (OV, BLCA, and SKCM), a core 105 proneural gene signature was identified. See FIG. 4.

Figure 5:
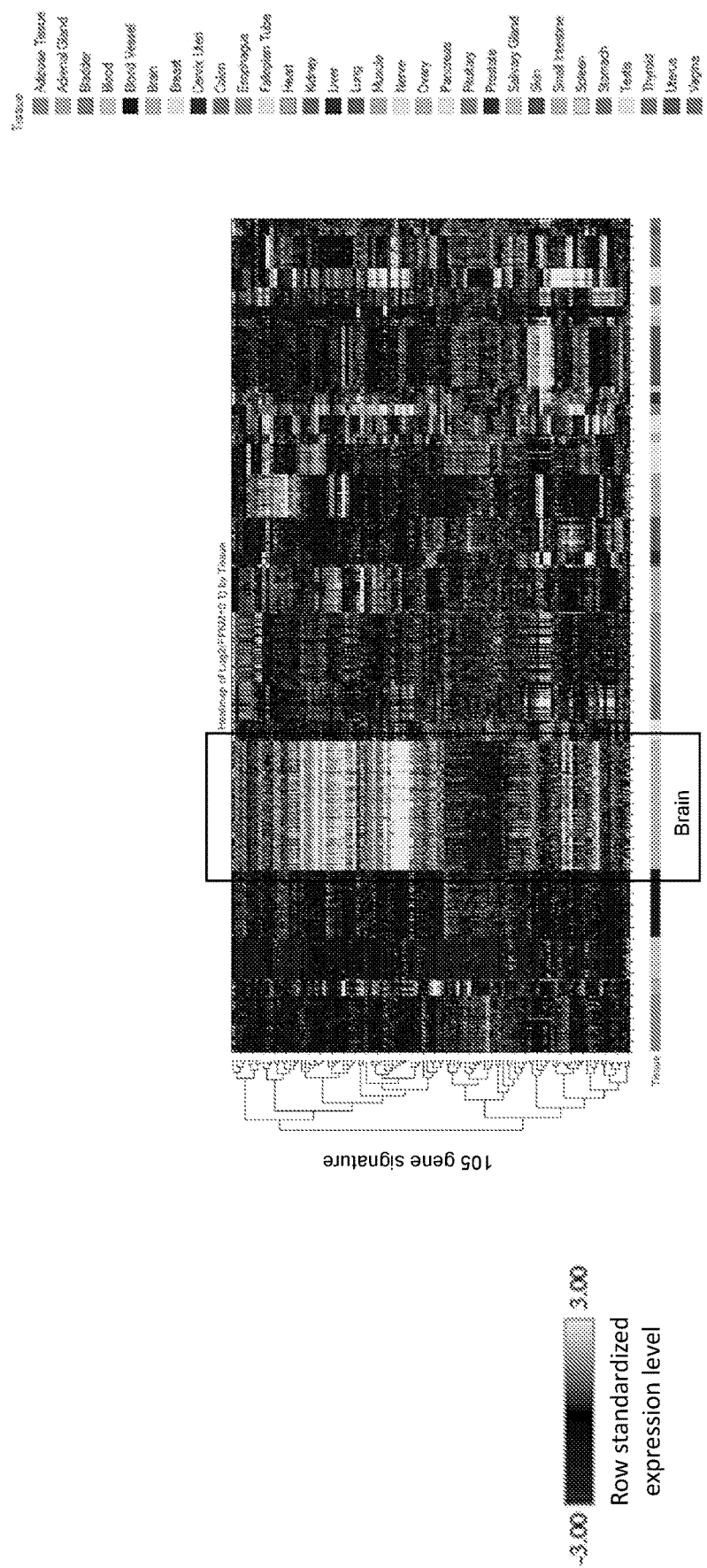
FIG. 5 shows that the proneural T-cell exclusion gene signature is enriched in normal brain. The heatmap in FIG. 5 shows the 105 proneural T-cell exclusion genes (each row is a gene and each column is a normal tissue sample from GTEx. The color shows the relative expression of that gene in a sample).
Figure 6A:
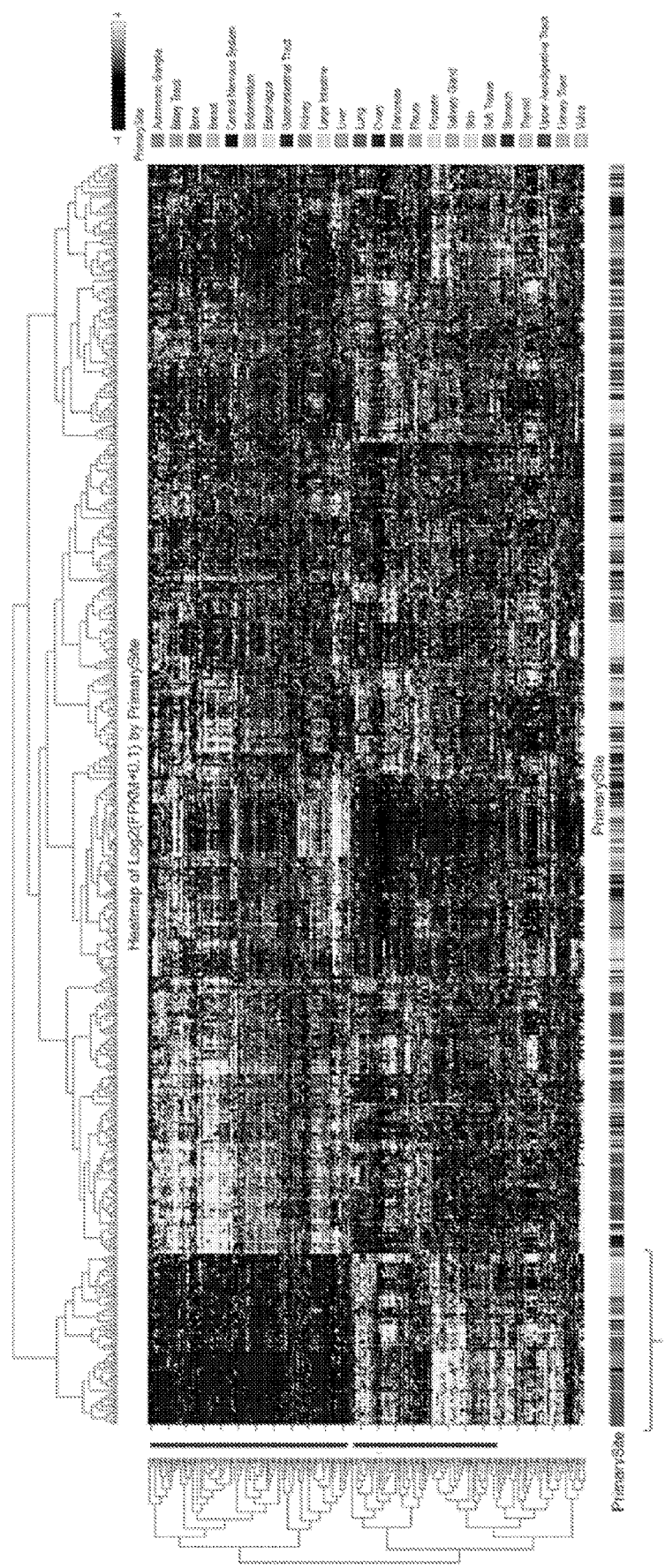
FIG. 6A shows a heatmap demonstrating a hierarchical clustering of cold tumor and interferon response genes for a subset of cancer cells lines from the cancer cell line encyclopedia (CCLE). The figure demonstrates that a subset of cancer cell lines carrying cold gene signature show high expression of the cold tumor genes (marked with red bar on the left of the figure) and low expression of interferon response genes (marked with blue bar on the left of the figure). This demonstrates evidence for a relationship between high expression of cold tumor genes and low expression of interferon response genes in at least cultured cancer cell lines. The high vs low expression is relative to the other samples or to a set of control samples.

FIG. 5 shows that the proneural T-cell exclusion gene signature is enriched in normal brain. The heatmap in FIG. 5 shows the 105 proneural T-cell exclusion genes (each row is a gene and each column is a normal tissue sample from GTEx, the color shows the relative expression of that gene in a sample). 50% of the genes show highest expression in the brain, and 60% of the genes show higher expression in proneural GBM compared to other GBM subtypes (TCGA, data not shown). FIG. 6A shows a heatmap demonstrating that a subset of cancer cells lines have high expression of the proneural signature and low expression of interferon response genes, and FIG. 6B shows a graph of proneural exclusion vs IFNG response.

FIG. 7A shows KDM1A (LSD-1) is more highly expressed in normal tissues compared to RCOR2. In FIG. 7B, RCOR2 shows a greater dynamic range of expression than LSD1 across different cancer types.

TABLE 2

Additional genes associated with "cold" tumors are involved in regulating histone and DNA methylation.

| Symbol | Name | Notes |
| --- | --- | --- |
| RCOR2 | REST corepressor 2 | Activates KDM1A |
| KDM1A | lysine (K)-specific demethylase 1A | H3K4 demethylase |
| CHD7 | chromodomain helicase DNA binding protein 7 | Interactes with H3K4me |
| CHD4 | chromodomain helicase DNA binding protein 4 | Chromatin remodeler, modulates H3K4me levels |
| CHD6 | chromodomain helicase DNA binding protein 6 | Chromatin remodeler |
| MBTD1 | mbt domain containing 1 | Stabilizes H3K4me1 and H3K20me1 |
| TET1 | tet methylcytosine dioxygenase 1 | DNA methylation |
| TET3 | tet methylcytosine dioxygenase 3 | DNA methylation |
| CBX2 | chromobox homolog 2 | chromatin remodeling and modification of histones |

The 105 proneural gene signature includes the following 105 genes: AK056486, NKAIN1, FAM183A, SAMD13, LINC00622, CHRNB2, MEX3A, IGSF9, C1ORF192, CCDC181, OCLM, PPFIA4, PANK1, B4GALNT4, GAS2, MS4A8, MYRF, RCOR2, FLRT1, AK313893, NXPH4, BC073932, MSI1, CCDC169, FREM2, ATP7B, AF339817, AK124233, GPX2, PAR5, PLA2G4F, IGDCC3, GOLGA6L10, UBE2Q2P2, WDR93, PDIA2, CASKIN1, AK096982, TOX3, AK057689, C16ORF3, AK127378, EFNB3, DNAH2, ANKRD13B, SOCS7, RAMP2-AS1, FAM171A2, ADAM11, METAZOA_SRP_75, CBX2, ZNF850, LOC100379224, TTYH1, VN1R1, MEIS1-AS3, LONRF2, BCO22892, KLHL23, AX747067, CCDC108, IRS1, KIF1A, FLRT3, SIM2, IGSF5, CECR5-AS1, FAM227A, AX747137, FGD5P1, ACVR2B, LOC646903, FGFR3, FLJ13197, SLC10A4, TTC23L, MCIDAS, GUSBP9, GPR98, SEMA6A, PCDHGC4, USP49, TMEM151B, AK125212, PACRG, AK123300, COL28A1, SOSTDC1, AK098769, FKBP6, DPY19L2P4, EPO, CTTNBP2, KIAA1549, TAS2R5, FAM86B2, DQ595103, CHD7, AK094577, WNK2, TMEFF1, AL390170, MUM1L1, HS6ST2, and PNCK. The 105 proneural gene signature is similar to the proneural gene signature in glioblastoma (GBM), which includes 175 proneural genes.

In some aspects, the proneural gene signature includes the following 141 genes: CASKIN1, CBX2, CHD7, CHRNB2, CHRNG, EFNB3, FREM2, KCNMB2, KDM1A, KDM5B, KIAA1549, KIF1A, LRP4, MEX3A, MSI1, NKAIN1, ONECUT2, OTUD3, RCOR2, RIMKLA, SBK1, SOCS7, TET3, TMEFF1, WNK2, ACVR2B, ADAM11, ADAMTS20, ALX3, ANKRD13B, ATP7B, B4GALNT4, C16orf3, C1orf192, CCDC108, CCDC150, CCDC169, CCDC181, CDH8, CECR2, CENPV, CNTNAP5, COL28A1, COL6A4P1, CTTNBP2, DNAH2, DNAJB7, EPO, FAM171A2, FAM183A, FAM227A, FAM84A, FAM86B2, FGD5P1, FGF12, FGFR3, FKBP6, FLJ13197, FLRT1, FLRT3, FSIP2, GAS2, GDF11, GOLGA6L10, GPR125, GPR98, GPX2, GUSBP9, HOXC13, HS6ST2, IGDCC3, IGSF11, IGSF5, IGSF9, INA, IRS1, ISM2, KC6, KIAA1804, KLHL11, KLHL23, LINC00470, LINC00622, LOC100379224, LOC100631378, LOC148709, LOC641515, LOC646903, LONRF2, LPHN3, MCIDAS, MED12L, MS4A8, MUM1L1, MYRF, NKPD1, NRG4, NXPH4, OCLM, PACRG, PANK1, PAR5, PARD6G, PCDHB11, PCDHGA1, PCDHGC4, PDIA2, PGAP1, PIANP, PLA2G4F, PLCB1, PLCE1, PNCK, PPFIA4, PPM1L, SAMD13, SEMA6A, SERPINB12, SIM2, SLC10A4, SLC30A10, SLC9A4, SLCO1A2, SOSTDC1, STOX2, SYT14, SYT2, TAS2R5, TMEM151B, TOX3, TRIM45, TTC23L, TTYH1, UBE2Q2P2, USP49, VN1R1, WDR72, WDR93, ZBTB12, ZNF663, and ZNF850.

In some aspects, the patient's cancer cells exhibit an increase in the gene expression of at least about 10% or at least about 15% of the genes where expression levels are measured. In some aspects, the patient's cancer cells exhibit an increase in the gene expression of at least about 20%, at least about 25%, at least about 30%, or at least about 35% of the genes where expression levels are measured. In some aspects, the patient's cancer cells exhibit an increase in the gene expression of at least about 20%, at least about 25%, at least about 30%, at least about 35%, at least about 40%, at least about 45%, at least about 50%, at least about 55%, at least about 60%, at least about 65%, at least about 70%, or at least about 75% of the genes where expression levels are measured. In some aspects, the patient's cancer cells exhibit an increase in the gene expression of at least about 60%, at least about 65%, at least about 70%, at least about 75%, at least about 80%, or at least about 85% of the genes where expression levels are measured. In some aspects, the patient's cancer cells exhibit an increase in the gene expression of at least about 90% of the genes where expression levels are measured.

In some aspects, a subset of the proneural signature genes, referred to herein as SCLC_20, are utilized as indicia of cold tumor types. The SCLC_20 proneural signature genes are as follows: RCOR2, NKAIN1, MSI1, CBX2, IGDCC3, GPC2, CECR2, KLHL23, TMEFF1, MEX3A, KIAA1549, FAM171A2, CENPV, INA, TMEM151B, KIF1A, SYT14, ONECUT2, KDM1A, and CHRNB2. In some aspects, indicia of a cold tumor include a high or increased expression of one or more of the SCLC_20 proneural signature genes. In some aspects, indicia of a cold tumor include a high or increased expression of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty of the SCLC_20 proneural signature genes. In some aspects, the high or increased expression of the SCLC_20 is relative to a control sample. In some aspects, the control sample lacks cold tumor cells.

In some aspects, a subset of the proneural signature genes, referred to as subset 1, comprises or consists of RCOR2, MSI1, CBX2, IGDCC3, TMEFF1, MEX3A, KIAA1549, FAM171A2, KIF1A, KDM5B, SBK1, LRP4, TET3, CASKIN1, NKAIN1, KDM1A, CECR2, KLHL23, CENPV, TMEM151B. In some aspects, indicia of a cold tumor include a high or increased expression of one or more of the subset 1 proneural signature genes. In some aspects, indicia of a cold tumor include a high or increased expression of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty of the subset 1 proneural signature genes. In some aspects, the high or increased expression of subset 1 proneural signature genes is relative to a control sample. In some aspects, the control sample lacks cold tumor cells.

In some aspects, the expression values derived from RNA sequencing for the individual genes in the signature are used in combination to generate an aggregate composite score using a method such as single-sample gene set enrichment analysis (ssGSEA) [Barbie et al. (2009) Systematic RNA interference reveals that oncogenic KRAS-driven cancers require TBK1. *Nature,* 462: 108-112.] using, for example, the GSVA R package (Hänzelmann et al., (2013). "GSVA: gene set variation analysis for microarray and RNA-Seq data." BMC Bioinformatics, 14, 7. doi: 10.1186/1471-2105-14-7, [[www]].biomedcentral.com/1471-2105/14/7]. In some aspects, a cold cancer tumor defined by a proneural signature is a tumor having an aggregate proneural ssGSEA score of greater than −0.05. In some aspects, a cold cancer tumor defined by a proneural signature is a tumor having an aggregate proneural ssGSEA score of at least −0.05, at least −0.06, at least −0.07, at least −0.08, at least −0.09, at least −0.1, at least −0.15, at least −0.2, at least −0.25, at least −0.3, at least −0.35, at least −0.4, at least −0.45, at least −0.5, at least −0.55, at least −0.6, at least −0.65, at least −0.7, at least −0.75, at least −0.8, at least −0.85, at least −0.9, or at least −0.95. In some aspects, a cold cancer tumor defined by a proneural signature is a tumor having an aggregate proneural ssGSEA score of between −0.05 to −0.95, −0.05 to −0.55, −0.55 to −0.95, −0.1 to −0.25, −0.25 to −0.55, or −0.75 to −0.95.

In some aspects, the aggregate proneural ssGSEA score is calculated based upon the interferon response genes of subset A, described below. In some aspects, the aggregate proneural ssGSEA score is calculated based upon at least 20%, at least 30%, at least 40%, at least 50%, at least 60%, at least 70%, at least 80%, or at least 90% of the interferon response genes of subset A.

In some aspects, the aggregate proneural ssGSEA score is calculated based upon the 200 interferon response genes described below. In some aspects, the aggregate proneural ssGSEA score is calculated based upon at least 20%, at least 30%, at least 40%, at least 50%, at least 60%, at least 70%, at least 80%, or at least 90% of the 200 interferon response genes described below.

GSEA is a method designed to assess the concerted behavior of functionally related genes forming a set, between two well-defined groups of samples, in this case based upon RNA sequencing data. Because it does not rely on a "gene list" of interest but on the entire ranking of genes, GSEA has been show to provide greater sensitivity to find gene expression changes of small magnitude that operate coordinately in specific sets of functionally related genes. ssGSEA calculates a gene set enrichment score per sample as the normalized difference in empirical cumulative distribution functions of gene expression ranks inside and outside a gene set.

In some aspects, some of the cold cell lines have high expression of the (1) proneural signature, (2) SCLC proneural signature, and/or (3) subset 1 proneural signature and low expression of interferon response genes.

The interferon response genes include: AC124319.1, ADAR, APOL6, ARID5B, ARL4A, AUTS2, B2M, BANK1, BATF2, BPGM, BST2, BTG1, C1R, C1S, CASP1, CASP3, CASP4, CASP7, CASP8, CCL2, CCL5, CCL7, CD274, CD38, CD40, CD69, CD74, CD86, CDKN1A, CFB, CFH, CIITA, CMKLR1, CMPK2, CMTR1, CSF2RB, CXCL10, CXCL11, CXCL9, DDX58, DDX60, DHX58, EIF2AK2, EIF4E3, EPSTI1, FAS, FCGR1A, FGL2, FPR1, GBP4, GBP6, GCH1, GPR18, GZMA, HELZ2, HERC6, HIF1A, HLA-A, HLA-B, HLA-DMA, HLA-DQA1, HLA-DRB1, HLA-G, ICAM1, IDO1, IFI27, IFI30, IFI35, IFI44, IFI44L, IFIH1, IFIT1, IFIT2, IFIT3, IFITM2, IFITM3, IFNAR2, IFL10RA, IL15, IL15RA, IL18BP, IL2RB, IL4R, IL6, IL7, IRF1, IRF2, IRF4, IRF5, IRF7, IRF8, IRF9, ISG15, ISG20, ISOC1, ITGB7, JAK2, KLRK1, LAP3, LATS2, LCP2, LGALS3BP, LYSE, LYSMD2, 1-MAR, METTL7B, MT2A, MEHFD2, MVP, MX1, MX2, MYD88, NAMPT, NCOA3, NFKB1, NFKBIA, NLRC5, NMI, NOD1, NUP93, OAS2, OAS3, OASL, OGFR, P2RY14, PARP12, PARP14, PDE4B, PELI1, PFKP, PIM1, PLA2G4A, PLSCR1, PML, PNP, PNPT1, PSMA2, PSMA3, PSMB10, PSMB2, PSMB8, PSMB9, PSME1, PSME2, PTGS2, PTPN1, PTPN2, PTPN6, RAPGEF6, RBCK1, RIPK1, RIPK2, RNF31, RSAD2, RTP4, SAMD9L, SAMHD1, SECTM1, SELP, SERPING1, SLAMF7, SLC25A28, SOCS1, SOCS3, SOD2, SP110, SPPL2A, SRI, SSPN, ST3GAL5, ST8SIA4, STAT1, STAT2, STAT3, STAT4, TAP1, TAPBP, TDRD7, TNFAIP2, TNFAIP3, TNFAIP6, TNFAIP10, TOR1B, TRAFD1, TRIM14, TRIM 21, TRIM25, TRIM 26, TXNIP, UBE2L6, UPP1, USP18, VAMP5, VAMP8, VCAM1, WARS, XAF1, XCL1, ZBP1, and ZNFX1.

In some aspects, a subset of the interferon response genes, referred to as subset A, include B2M, APOL6, CD86, IL15, IRF1, LCP2, CASP1, PSMB10, HLA-DMA, CD74, IL15RA, HLA-DRB1, FGL2, HLA-B, KLRK1, IL7, STAT4, CIITA, IL10RA, and SAMD9L.

In some aspects, the low expression of the interferon response genes and/or the interferon response gene subset A is a single-sample gene set enrichment analysis (ssGSEA) aggregate score of less than 0.2. In some aspects, the low expression of the interferon response genes and/or the interferon response gene subset A is a ssGSEA aggregate score of less than 0.2, less than 0.175, less than 0.15, less than 0.125, less than 0.1, less than 0.075, less than 0.05, less than 0.025, or less than 0.001. In some aspects, the low expression of the interferon response genes and/or the interferon response gene subset A is a ssGSEA aggregate score of between 0.001 to 0.2, 0.001 to 0.175, 0.001 to 0.15, 0.001 to 0.125, 0.001 to 0.1, 0.001 to 0.075, 0.001 to 0.025, 0.025 to 0.2, 0.025 to 0.175, 0.025 to 0.15, 0.025 to 0.125, 0.025 to 0.1, 0.025 to 0.075, 0.025 to 0.05, 0.05 to 0.2, 0.05 to 0.175, 0.05 to 0.15, 0.05 to 0.125, 0.05 to 0.1, 0.05 to 0.075, 0.075 to 0.2, 0.075 to 0.15, 0.075 to 0.1, 0.1 to 0.2, 0.1 to 0.175, 0.1 to 0.15, 0.1 to 0.125, 0.125 to 0.2, 0.125 to 0.175, 0.125 to 0.15. 0.15 to 0.2, 0.15 to 0.175, and 0.175 to 0.2.

In some aspects, a lack of expression of one or more of the interferon response genes amounts to no measurable expression of, for example AC123419.1 protein/mRNA when measured by any means of determining protein expression and RNA.

In some aspects, the patient's cancer cells exhibit a decrease in the gene expression of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the interferon response genes where expression levels are measured.

In some aspects, preferred cancer patient populations are identified as those that comprise one or more "cold" tumors that are diagnostic positive for low immune cell infiltrate in one or more tumors. In some aspects, low immune cell infiltrate is the decrease or absence of lymphocytes. In some aspects, low immune cell infiltrate is the decrease or absence of tumor-infiltrating lymphocytes (TILs). In some aspects, low immune cell infiltrate is the decrease or absence of dendritic cells. In some aspects, low immune cell infiltrate is the decrease or absence of myeloid cells. In some aspects, low immune cell infiltrate is the decrease or absence of NK cells. In some aspects, low immune cell infiltrate is the decrease or absence of macrophages. In some aspects, low immune cell infiltrate is the decrease or absence of T cells. In some aspects, low immune cell infiltrate is the decrease or absence of CD8+ T cells. In some aspects, low immune cell infiltrate is the decrease or absence of CD4+ T cells. In some aspects, low immune cell infiltrate is the decrease or absence of CD4+/CD8+ T cells.

In some aspects, low immune cell infiltrate is the decrease or absence of lymphocytes, TILs, dendritic cells, myeloid cells, macrophages, T cells, CD8+ T cells, CD4+ T cells, and/or CD8+/CD4+ T cells.

In some aspects, the low immune cell infiltrate is at least about 10%, about 20%, about 30%, about 40%, about 50%, about 55%, about 60%, about 65%, about 70%, about 75%, about 80%, about 85%, about 90%, or about 95% decrease in the amount of immune cell infiltrate in one or more tumors. In some aspects, the decrease is measured relative to a control, a "hot" tumor or a non-"cold" tumor.

In some aspects, the tumor-infiltrating lymphocytes (TILs) are CD4+ lymphocytes. In some aspects, the TILs are CD8+ lymphocytes. In some aspects, the TILs are both CD4+ and CD8+ lymphocytes. In some aspects, the TILs are CD4− T cells. In some aspects, the TILs are CD8−TILs. In some aspects, the TILs are CD4−/CD8−.

In some aspects, the presence of immune cell infiltrate within the tumor is measured or estimated by gene expression levels of T cell markers in bulk RNA profiling data. In some aspects, the immune cell infiltrate within the tumor is measured by cell sorting methods. In some aspects, the immune cell infiltrate is measured by immunohistochemistry methods. In some aspects, the immune cell infiltrate is measured by immunohistochemistry methods utilizing formalin-fixed paraffin-embedded tissue (FFPE).

In some aspects, preferred cancer patient populations are identified as those that comprise one or more "cold" cancer tumors that are diagnostic positive for RCOR2 expression or increased RCOR2 expression relative to a control tissue or a non-"cold" tumor. RCOR2, also known as REST corepressor 2 (CoREST2), was found to be the most highly correlated with T cell Exclusion genes across cold tumor types. In some aspects, with regard to normal tissue, RCOR2 exhibits the highest expression in the brain, specifically the cortex, with particularly high expression in proneural glioblastoma. RCOR2-LSD1 complex is known to regulate histone H3 lysine 4 demethylation.

In some aspects, the one or more tumors exhibit an increased expression in RCOR2 by at least about 10%, about 20%, about 30%, about 40%, about 50%, about 55%, about 60%, about 65%, about 70%, about 75%, about 80%, about 85%, about 90%, about 95%, about 100%, about 125%, about 150%, about 175%, about 200%, about 300%, about 400%, or about 500% relative to a control tissue.

In some aspects, RCOR2 expression is measured by bulk mRNA expression, such as by RNA sequencing or Quantigene. In some aspects, RCOR2 expression is measured by bulk RNA expression using Quantigene. In some aspects, an RCOR2 positive tumor is defined by RCOR2 mRNA score of greater than 0.055. In some aspects, the RCOR2 mRNA score is normalized to geometric mean of control genes. In some aspects, the RCOR2 mRNA score is normalized to geometric mean of control genes PPIB, GUSB, HPRT1 in SCLC cell lines. In some aspects, the RCOR2 positive tumor is defined by an RCOR2 mRNA score of at least 0.055, at least 0.06, at least 0.065, at least 0.070, at least 0.075, at least 0.080, at least 0.085, at least 0.090, at least 0.095, at least 0.1, at least 0.125, at least 0.15, at least 0.175, at least 0.2, at least 0.225, at least 0.25, at least 0.275, at least 0.3, at least 0.35, at least 0.4, at least 0.45, at least 0.5, at least 0.55, at least 0.6, at least 0.65, at least 0.7, at least 0.75, at least 0.8, at least 0.85, at least 0.9, or at least 0.85. In some aspects, the RCOR2 positive tumor is defined by an RCOR2 mRNA score of between 0.055 to 0.95, 0.055 to 0.1, 0.1 to 0.95, 0.1 to 0.5, 0.25 to 0.95, 0.25 to 0.5, 0.5 to 0.95, 0.5 to 0.75, 0.75 to 0.95.

In some aspects, the control gene is a housekeeping gene such as GAPDH, ACTB, etc. In some aspects, the control gene or control genes are utilized to make a relative determination of high expression, low expression, or no change in expression in protein expression, mRNA, etc.

In some aspects, RCOR2 expression is measured by protein expression, such as by immunohistochemistry (IHC) or immunofluorescense.

In some aspects, an RCOR2 positive tumor is defined by an RCOR2 protein expression value (nuclear H score) greater than 60. In some aspects, the RCOR2 protein expression value is determined with immunohistochemistry. In some aspects, an RCOR2 positive tumor exhibits an RCOR2 protein expression value of at least 60, at least 65, at least 70, at least 75, at least 80, at least 85, at least 90, or at least 95. In some aspects, an RCOR2 positive tumor exhibits an RCOR2 protein expression value of between 60 to 95, 60 to 90, 60 to 85, 60 to 80, 60 to75, 60 to 70, 60 to 65, 65 to 90, 65 to 85, 65 to 80, 65 to 75, 65 to 70, 70 to 95, 70 to 90, 70 to 85, 70 to 80, 70 to 75, 75 to 95, 75 to 90, 75 to 85, 75 to 80, 80 to 95, 80 to 90, 80 to 85, 85 to 95, 85 to 90, or 90 to 95.

In some aspects, the H-score (range of 0-300) are the sum of the products of each intensity value multiplied by the percentage of cells at that intensity to account for 100% of the tumor cells.

H-score=(% at 1+)*1+(% at 2+)*2+(% at 3+)*3. 0=negative, 1=weak, 2=moderate, 3=strong. In some aspects, the H-score is the median H-score In some aspects, an RCOR2 positive tumor is defined by an RCOR2 bulk mRNA expression value from RNA sequencing normalized for GAPDH expression greater than −7.5 (RCOR2 log 2 TPM-GAPDH log 2 TPM). TPM=transcript count per million.

V. Pharmaceutical Compositions

In one aspect, the compound used in the methods described herein is the compound of Formula (I), which has the following structure:

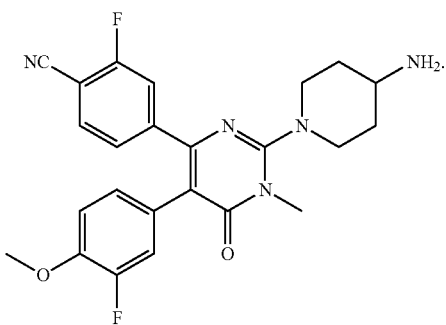

In another aspect, the compound used in the methods described herein is a pharmaceutically acceptable salt, such as but not limited to a benzenesulfonic acid salt (also known as besylate salt) of the compound of Formula (I).

In some aspects, a composition of the present disclosure consists of or consists essentially of the compound of Formula (I) or a pharmaceutically acceptable salt thereof, such as a besylate salt thereof. In some aspects, a composition of the present disclosure consists of or consists essentially of the compound of Formula (I) and a pharmaceutically acceptable salt thereof, such as a besylate salt thereof. In some aspects, a composition of the present disclosure comprises the compound of Formula (I) or a pharmaceutically acceptable salt thereof, such as a besylate salt thereof. In some aspects, a composition of the present disclosure comprises the compound of Formula (I) and a pharmaceutically acceptable salt thereof, such as a besylate salt thereof.

In other aspects, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in REMINGTON: THE SCIENCE & PRACTICE OF PHARMACY (Gennaro, 21$^{st}$ Ed. Mack Pub. Co., Easton, PA (2005)).

Provided herein is a pharmaceutical composition comprising the compound of Formula (I) or a pharmaceutically acceptable salt thereof, such as a besylate salt thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, such as a besylate salt thereof, and a pharmaceutically acceptable excipient.

In certain embodiments, the compound of Formula (I) is substantially pure, in that it contains less than about 5%, or less than about 1%, or less than about 0.1%, of other organic small molecules, such as unreacted intermediates or synthesis by-products that are created, for example, in one or more of the steps of a synthesis method.

In some aspects, the pharmaceutical composition is formulated for oral dosage or injectable dosage. In some aspects, suitable oral dosage forms include, for example, tablets, pills, sachets, or capsules of hard or soft gelatin, methylcellulose or of another suitable material easily dissolved in the digestive tract. In some aspects, a suitable injectable dosage is an injectable solution comprising one or more of the compounds described herein. In some aspects, the injectable solution is an injectable solution for intravenous injection.

In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., REMINGTON: THE SCIENCE & PRACTICE OF PHARMACY (Gennaro, 21$^{st}$ Ed. Mack Pub. Co., Easton, PA (2005)).

In some aspects, (a) the compound of Formula (I) or a pharmaceutically acceptable salt thereof, such as a besylate salt thereof, is an inhibitor of Lysine-specific histone demethylase 1 (LSD-1); and/or (b) the compound of Formula (I) or a pharmaceutically acceptable salt thereof, such as a besylate salt thereof, is a reversible antagonist to LSD-1; and/or (c) the compound of Formula (I) or a pharmaceutically acceptable salt thereof, such as a besylate salt thereof, is a reversible inhibitor of LSD-1. In some aspects, when the LSD-1 is blocked, infiltration of T cells is thereby enabled, thus allowing a CPI, which can be an anti-PDL1 and/or anti-PD1 therapy, to retard tumor growth and/or reduce tumor size. In some aspects, LSD-1 is inhibited from demethylating histone complexes, and thereby infiltration of T cells is enabled, thus allowing CPI therapy, which can be anti-PDL1 and/or anti-PD1 therapy, to retard tumor growth and/or tumor size. In some aspects, LSD-1 is prevented from forming a functional protein complex with RCOR2, and thereby infiltration of T cells is enabled, thus allowing CPI therapy, which can be anti-PDL1 and/or anti-PD1 therapy, to retard tumor growth and/or tumor size. In some aspects, the subject's cancer has a high non-synonymous mutational burden.

In some aspects, (a) the composition further comprises a therapeutically effective amount of etoposide; or (b) an additional composition comprising a therapeutically effective amount of etoposide is administered. In some aspects, (a) the composition further comprises a therapeutically effective amount of a platin, and optionally wherein the platin is selected from the group consisting of cisplatin, carboplatin, exaliplatin, nedaplatin, triplatin tetranitrate, phenanthriplantin, picoplatin, and satraplatin; or (b) an additional composition comprising a therapeutically effective amount of a platin is administered, and optionally wherein the platin is selected from the group consisting of cisplatin, carboplatin, exaliplatin, nedaplatin, triplatin tetranitrate, phenanthriplantin, picoplatin, and satraplatin.

VI. Treating Diagnostic Positive "Cold" Tumors

In some aspects, the present disclosure is drawn to methods of treating cancer in a patient in need thereof, comprising administering to the patient the compound of Formula (I) or a pharmaceutically acceptable salt thereof, such as a besylate salt thereof. In all of the methods described herein, a CPI can additionally be administered to the subject. In some aspects, the patient in need thereof is a patient that is diagnostic positive for one or more "cold" tumors, as identified by the indicia described herein—(1) increased RCOR2 expression, (2) low interferon response gene signature, (3) decreased or no tumor immune infiltrate, and/or (4) high proneural gene signature. In some aspects, the patient in need thereof is a patient that is diagnostic positive for one or more "cold" tumors, as identified by increased RCOR2 expression and/or high proneural gene signature.

In some aspects, administering the compound of Formula (I) or a pharmaceutically acceptable salt thereof to a patient comprising a "cold" tumor results in the "cold" tumor transforming into a "hot" tumor. In some aspects, the transformation of the "cold" tumor into a "hot" tumor allows for immune cell infiltrate into the tumor to retard growth of the tumor, decrease the size/volume of the tumor, and/or destroy the tumor. In some aspects, the transformation of the "cold" tumor into a "hot" tumor allows for concomitant therapy with one or more CPIs, such as PD1, to be effective, even in tumor types that were initially insensitive to CPI therapy or became insensitive to CPI therapy.

In further aspects, methods are provided for the treatment of relapsed and/or refractory solid tumors (including neuroendocrine carcinomas (NEC), pheochromocytoma, and Merkel cell cancer) and non-Hodgkin's lymphomas (NHLs) and the like, using the compound of Formula (I) or a pharmaceutically acceptable salt thereof, such as a besylate salt thereof, and pharmaceutical compositions comprising the same useful for the inhibition of lysine specific demethylase-1 (LSD-1). Relapse refers to the return of a disease or the signs and symptoms of a disease after a period of improvement. Refractory refers to a disease or condition that does not respond to treatment. Refractory cancer refers to cancer that does not respond to treatment and includes circumstances where the cancer may be resistant at the beginning of treatment or the cancer becomes resistant during treatment.

Examples of cancer and neoplastic disease include, for example, advanced solid tumors, relapsed or refractory solid tumors (including neuroendocrine carcinomas (NEC) and non-Hodgkin's lymphomas), glioblastoma multiforme, anaplastic astrocytoma, basal cell carcinoma, lung cancer, small cell lung cancer (SCLC), lung squamous cell carcinoma (LUSC), head and neck squamous cell carcinoma (HNSC), HPV-negative head and neck squamous cell carcinoma (HNSC HPV neg), bladder carcinoma (BLCA), bladder urothelial carcinoma, melanoma, skin cutaneous melanoma (SKCM), breast cancer, triple negative breast cancer (TNBC), ovarian cancer (OV), stomach cancer, stomach adenocarcinoma (STAD), carcinoma (SARC), prostate cancer, and marginal zone lymphoma.

In some aspects, the patient has a cancer selected from the group consisting of lung cancer, small cell lung cancer (SCLC), lung squamous cell carcinoma (LUSC), head and neck squamous cell carcinoma (HNSC), HPV-negative head and neck squamous cell carcinoma (HNSC HPV neg), bladder carcinoma (BLCA), bladder urothelial carcinoma, melanoma, skin cutaneous melanoma (SKCM), breast cancer, triple negative breast cancer (TNBC), ovarian cancer (OV), stomach cancer, stomach adenocarcinoma (STAD), sarcomas (SARC), neuroendocrine tumors, advanced solid tumors, prostate cancer, and marginal zone lymphoma.

In some aspects, the patient has a cancer selected from the group consisting of melanoma, metastatic non-small cell lung cancer, head and neck squamous cell carcinoma, squamous cell lung cancer, renal cell carcinoma, Hodgkin's lymphoma, cutaneous squamous cell carcinoma (CSCC), patients with locally advanced CSCC who are not candidates for curative surgery or curative radiation, solid tumors and lymphomas, relapsed or refractory classical Hodgkin lymphoma, small cell lung cancer (SCLC), solid tumors and hematologic cancers.

In some aspects, methods are drawn to regulating gene transcription in a cell or in a subject, the method comprising inhibiting lysine-specific demethylase 1 activity by exposing the lysine-specific demethylase 1 enzyme to the compound of Formula (I) or a pharmaceutically acceptable salt thereof, such as a besylate salt thereof.

In some aspects, methods are drawn to modulating demethylation in a cell or in a subject, either generally or with respect to one or more specific target genes. Demethylation is modulated to control a variety of cellular functions, including without limitation: differentiation; proliferation; apoptosis; tumorigenesis, leukemogenesis or other oncogenic transformation events; hair loss; or sexual differentiation.

In some aspects, the present disclosure is drawn to methods of treating cancer in a subject in need thereof, comprising identifying a cancer patient having "cold" tumors comprising cells that exhibit (1) increased RCOR2 expression, (2) low interferon response gene signature, (3) decreased or no tumor immune infiltrate, and/or (4) high proneural gene signature; and administering to the patient a composition of the present disclosure. In some aspects, the composition comprises the compound of Formula (I) or a pharmaceutically acceptable salt thereof, such as a besylate salt thereof. The method can additionally comprise administering a CPI.

In some aspects, a method of identifying cancer cells that exhibit (1) increased RCOR2 expression, (2) low interferon response gene signature, (3) decreased or no tumor immune infiltrate, and/or (4) high proneural exclusion gene signature comprises isolating the cancer cells or a sample comprising the cancer cells. In some aspects, the sample is a blood sample, lymph sample, and/or a tissue sample. In some aspects, a determination of RCOR2 expression, interferon response gene signature, and/or proneural exclusion gene signature is a determination of the amount of mRNA encoding (1) RCOR2, (2) the genes of the interferon response gene signature, and/or (3) the genes of the proneural exclusion gene signature. In some aspects, a determination of RCOR2 expression, interferon response gene signature, and/or proneural exclusion gene signature is a determination of the amount of (1) RCOR2 expression, (2) the gene products of the interferon response gene signature genes, and/or (3) the gene products of the proneural exclusion gene signature genes. In some aspects, the gene products are proteins.

In some aspects, the method of treating cancer in a subject in need thereof comprises identifying a cancer patient having cancer cells that exhibit high expression of RCOR2 or high transcription of mRNA encoding RCOR2, and administering to the patient a composition comprising a therapeutically effective amount of the compound of Formula (I) or a pharmaceutically acceptable salt thereof, such as a besylate salt thereof. The method can additionally comprise administering a CPI.

In some aspects, the method of treating cancer in a subject in need thereof comprises identifying a cancer patient having cancer cells that exhibit expression of the gene products of the interferon response gene signature genes or transcription of mRNA encoding the interferon response gene signature genes, and administering to the patient a composition comprising a therapeutically effective amount of the compound of Formula (I) or a pharmaceutically acceptable salt thereof, such as a besylate salt thereof. The method can additionally comprise administering a CPI.

In some aspects, the method of treating cancer in a subject in need thereof comprises identifying a cancer patient having cancer cells that exhibit expression of the gene products of the proneural signature genes or transcription of mRNA encoding the proneural signature genes, and administering to the patient a composition comprising a therapeutically effective amount of the compound of Formula (I) or a pharmaceutically acceptable salt thereof, such as a besylate salt thereof. The method can additionally comprise administering a CPI.

In some aspects, the method of treating cancer in a subject in need thereof comprises identifying a cancer patient having cancer cells that exhibit decreased or no tumor immune infiltrate, as compared to a "hot" tumor or a non-"cold" tumor, and administering to the patient a composition comprising a therapeutically effective amount of the compound of Formula (I) or a pharmaceutically acceptable salt thereof, such as a besylate salt thereof. The method can additionally comprise administering a CPI.

In some aspects, the cancer cells are one or more of the following cancers: lung cancer, small cell lung cancer (SCLC), lung squamous cell carcinoma (LUSC), head and neck squamous cell carcinoma (HNSC), HPV-negative head and neck squamous cell carcinoma (HNSC HPV neg), bladder carcinoma (BLCA), bladder urothelial carcinoma, melanoma, skin cutaneous melanoma (SKCM), breast cancer, triple negative breast cancer (TNBC), ovarian cancer (OV), stomach cancer, stomach adenocarcinoma (STAD), sarcomas (SARC), neuroendocrine tumors, advanced solid tumors, prostate cancer, and marginal zone lymphoma.

In some aspects, the subject or patient has failed one or more treatments with a CPI, such as an anti-programmed cell death protein 1 (PD1) therapy. In some aspects, the subject or patient has failed one or more treatments with a CPI, such as anti-programmed death-ligand 1 (PD-L1) therapy. In some aspects, failure of a therapy or treatment occurs when the cancer of the subject or patient does not respond to the therapy or treatment. In some aspects, failure of a therapy or treatment occurs when the cancer of the subject or patient initially responds to the therapy or treatment, but the therapy or treatment of the cancer is ineffective or considerably less effective in subsequent treatments.

In some aspects, the CPI therapy is selected from the group consisting of: (a) nivolumab; (b) pembrolizumab; (c) cemiplimab; (d) spartalizumab (e) camrelizumab; (f) sintilimab; (g) tislelizumab; (h) toripalimab; (i) AMP-224; (j) MEDI0680; (k) durvalumab; and (l) tislelizumab. In some aspects, the anti-PDL1 therapy is selected from the group consisting of: (a) atezolizumab; (b) avelumab; (c) durvalumab; (d) KN035; (e) CK-301; (f) CA-170; and (g) BMS-986189.

In some aspects, the patient's cancer exhibits a cold tumor signature. In some aspects, the patient's cancer exhibits a cold tumor signature. In some aspects, the patient's cancer does not respond, or has minimal response, to single agent CPI therapy.

In some aspects, the patient's cancer does not respond, or has minimal response, to single agent CPI therapy and the patient's cancer cells exhibit high expression of RCOR2 or high transcription of mRNA encoding RCOR2.

In some aspects, the patient's cancer does not respond, or has minimal response, to single agent CPI therapy. In some aspects, the patient's cancer does not respond, or has minimal response, to single agent CPI therapy and the patient's cancer cells exhibit expression of the gene products of the interferon response gene signature genes or transcription of mRNA encoding the interferon response gene signature genes.

In some aspects, the patient's cancer does not respond, or has minimal response, to single agent CPI therapy and the patient's cancer cells exhibit expression of the gene products of the proneural signature genes or transcription of mRNA encoding the proneural signature genes.

In some aspects, the patient's cancer does not respond, or has minimal response, to single agent CPI therapy and the patient's cancer cells exhibit decreased or non-detectable tumor immune infiltrate, as compared to a "hot" tumor or a non-"cold" tumor.

In some aspects, the patient's cancer does not respond, or has minimal response, to single agent CPI, and the patient's cancer exhibits one or more "cold" tumor signatures. In some aspects, the patient's cancer does not respond, or has minimal response, to single agent CPI, and the patient's cancer exhibits two or more "cold" tumor signatures. In some aspects, the patient's cancer does not respond, or has minimal response, to single agent CPI, and the patient's cancer exhibits three or more "cold" tumor signatures.

In some aspects, a cold tumor signature is defined by low or no CD8 T cell infiltration within a tumor. In some aspects, a cold tumor signature is defined by exhibition of T cell non-inflamed or T cell excluded states based on the presence of T cells within the tumor. In some aspects, a cold tumor signature is defined by low or no CD8 T cell infiltration within a tumor and exhibition of T cell non-inflamed or T cell excluded states based on the presence of T cells within the tumor.

In some aspects, the presence of T cells within the tumor is determined by measuring or estimating the gene expression levels of T cell markers from RNA profiling data or bulk RNA profiling data.

In some aspects, the patient's cancer cells exhibit an increase in the gene expression of one or more of the following genes: AK056486, NKAIN1, FAM183A, SAMD13, LINC00622, CHRNB2, MEX3A, IGSF9, C1ORF192, CCDC181, OCLM, PPFIA4, PANK1, B4GALNT4, GAS2, MS4A8, MYRF, RCOR2, FLRT1, AK313893, NXPH4, BC073932, MSI1, CCDC169, FREM2, ATP7B, AF339817, AK124233, GPX2, PAR5, PLA2G4F, IGDCC3, GOLGA6L10, UBE2Q2P2, WDR93, PDIA2, CASKIN1, AK096982, TOX3, AK057689, C16ORF3, AK127378, EFNB3, DNAH2, ANKRD13B, SOCS7, RAMP2-AS1, FAM171A2, ADAM11, METAZOA_SRP_75, CBX2, ZNF850, LOC100379224, TTYH1, VN1R1, MEIS1-AS3, LONRF2, BC022892, KLHL23, AX747067, CCDC108, IRS1, KIF1A, FLRT3, SIM2, IGSF5, CECR5-AS1, FAM227A, AX747137, FGD5P1, ACVR2B, LOC646903, FGFR3, FLJ13197, SLC10A4, TTC23L, MCIDAS, GUSBP9, GPR98, SEMA6A, PCDHGC4, USP49, TMEM151B, AK125212, PACRG, AK123300, COL28A1, SOSTDC1, AK098769, FKBP6, DPY19L2P4, EPO, CTTNBP2, KIAA1549, TAS2R5, FAM86B2, DQ595103, CHD7, AK094577, WNK2, TMEFF1, AL390170, MUM1L1, HS6ST2, and PNCK. In some aspects, the increase in the gene expression of the genes is relative to the gene expression of a control gene.

In some aspects, the patient's cancer cells exhibit an increase in the gene expression of one or more of the following genes: RCOR2, NKAIN1, MSI1, CBX2, IGDCC3, GPC2, CECR2, KLHL23, TMEFF1, MEX3A, KIAA1549, FAM171A2, CENPV, INA, TMEM151B, KIF1A, SYT14, ONECUT2, KDM1A, and CHRNB2.

In some aspects, the increase in the gene expression of the one or more genes is an increase of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the number of listed genes.

In some aspects, the increase in the gene expression of the one or more genes is an increase of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the number of listed genes.

In some aspects, the increase in the gene expression of the one or more genes is an increase of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the number of listed genes.

In some aspects, the increase in the gene expression of the one or more genes is an increase of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 125%, at least about 150%, at least about 175%, at least about 200%, at least about 250%, at least about 300%, at least about 350%, at least about 400%, or at least about 500%.

In some aspects, the increase in the gene expression of the one or more genes is an increase of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, at least 250%, at least 300%, at least 350%, at least 400%, or at least 500%.

In some aspects, the increase in the gene expression of the one or more genes is an increase of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 125%, about 150%, about 175%, about 200%, about 250%, about 300%, about 350%, about 400%, or about 500%.

In some aspects, the patient's cancer cells exhibit a decrease in the gene expression of one or more interferon response genes, wherein the decrease in the gene expression is relative to the gene expression of a control gene. In some aspects, the interferon response genes are selected from AC124319.1, ADAR, APOL6, ARID5B, ARL4A, AUTS2, B2M, BANK1, BATF2, BPGM, BST2, BTG1, C1R, C1S, CASP1, CASP3, CASP4, CASP7, CASP8, CCL2, CCL5, CCL7, CD274, CD38, CD40, CD69, CD74, CD86, CDKN1A, CFB, CFH, CIITA, CMKLR1, CMPK2, CMTR1, CSF2RB, CXCL10, CXCL11, CXCL9, DDX58, DDX60, DHX58, EIF2AK2, EIF4E3, EPSTI1, FAS, FCGR1A, FGL2, FPR1, GBP4, GBP6, GCH1, GPR18, GZMA, HELZ, HERC6, HIF1A, HLA-A, HLA-B, HLA-DMA, HLA-DQA1, HLA-DRB1, HLA-G, ICAM1, IDO1, IF127, IFI30, IFI35, IFI44, IFI44L, IFIH1, IFIT1, IFIT2, IFIT3, IFITM2, IFITM3, IFNAR2, IFL10RA, IL15, IL15RA, IL18BP, IL2RB, IL4R, IL6, IL7, IRF1, IRF2, IRF4, IRF5, IRF7, IRF8, IRF9, ISG15, ISG20, ISOC1, ITGB7, JAK2, KLRK1, LAP3, LATS2, LCP2, LGALS3BP, LYSE, LYSMD2, 1-MAR, METTL7B, MT2A, MEHFD2, MVP, MX1, MX2, MYD88, NAMPT, NCOA3, NFKB1, NFKBIA, NLRC5, NMI, NOD1, NUP93, OAS2, OAS3, OASL, OGFR, P2RY14, PARP12, PARP14, PDE4B, PELI1, PFKP, PIM1, PLA2G4A, PLSCR1, PML, PNP, PNPT1, PSMA2, PSMA3, PSMB10, PSMB2, PSMB8, PSMB9, PSME1, PSME2, PTGS2, PTPN1, PTPN2, PTPN6, RAPGEF6, RBCK1, RIPK1, RIPK2, RNF31, RSAD2, RTP4, SAMD9L, SAMHD1, SECTM1, SELP, SERPING1, SLAMF7, SLC25A28, SOCS1, SOCS3, SOD2, SP110, SPPL2A, SRI, SSPN, ST3GAL5, ST8SIA4, STAT1, STAT2, STAT3, STAT4, TAP1, TAPBP, TDRD7, TNFAIP2, TNFAIP3, TNFAIP6, TNFAIP10, TOR1B, TRAFD1, TRIM14, TRIM 21, TRIM25, TRIM 26, TXNIP, UBE2L6, UPP1, USP18, VAMP5, VAMP8, VCAM1, WARS, XAF1, XCL1, ZBP1, and ZNFX1.

In some aspects, the patient's cancer cells exhibit a decrease in the gene expression of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the interferon response genes.

In some aspects, the patient's cancer cells exhibit a decrease in the gene expression of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the interferon response genes.

In some aspects, the patient's cancer cells exhibit a decrease in the gene expression of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the interferon response genes.

In some aspects, the patient's cancer cells exhibit a decrease in the gene expression the interferon response by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some aspects, the patient's cancer cells exhibit a decrease in the gene expression the interferon response by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

In some aspects, the patient's cancer cells exhibit a decrease in the gene expression the interferon response by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some aspects, the compound of Formula (I) or a pharmaceutically acceptable salt thereof, such as a besylate salt thereof, is an inhibitor of lysine-specific histone demethylase 1 (LSD-1). In some aspects, the compound of Formula (I) or a pharmaceutically acceptable salt thereof, such as a besylate salt thereof, is a reversible antagonist to LSD-1. In some aspects, the compound of Formula (I) or a pharmaceutically acceptable salt thereof, such as a besylate salt thereof, is a reversible inhibitor of LSD-1. In some aspects, the compound of Formula (I) or a pharmaceutically acceptable salt thereof, such as a besylate salt thereof, is an inhibitor of lysine-specific histone demethylase 1 (LSD-1), is a reversible antagonist to LSD-1, and/or is a reversible inhibitor of LSD-1.

In some aspects, when LSD-1 is blocked, infiltration of T cells is thereby enabled, thus allowing CPI therapy, which can be anti-PDL1 and/or anti-PD1 therapy, to retard tumor growth and/or reduce tumor size.

In some aspects, when LSD-1 is inhibited from demethylating histone complexes, and thereby infiltration of T cells is enabled, thus allowing CPI therapy, which can be anti-PDL1 and/or anti-PD1 therapy, to retard tumor growth and/or tumor size. In some aspects, LSD-1 is prevented from forming a functional protein complex with RCOR2, and thereby infiltration of T cells is enabled, thus allowing CPI therapy, which can be anti-PDL1 and/or anti-PD1 therapy, to retard tumor growth and/or tumor size.

In some aspects, administration of the compound of Formula (I) or a pharmaceutically acceptable salt thereof, such as a besylate salt thereof, and CPI therapy (which can be an anti-PD1 therapy and/or an anti-PDLI therapy), results in infiltration of T cells in tumors that are diagnostic positive for "cold" tumors, wherein the T cell infiltration is an increase of at least about 10%, at least about 25%, at least about 75%, at least about 100%, at least about 125%, at least about 150%, at least about 175%, at least about 200%, at least about 250%, at least about 300%, at least about 400%, at least about 500%, at least about 600%, at least about 700%, at least about 800%, at least about 900%, or at least about 1000% as compared to T cell infiltration prior to administration or administration with a placebo.

In some aspects, administration of the compound of Formula (I) or a pharmaceutically acceptable salt thereof, such as a besylate salt thereof, and CPI therapy (which can be anti-PD1 therapy, and/or an anti-PDLI therapy), results in infiltration of T cells in tumors that are diagnostic positive for "cold" tumors, wherein the T cell infiltration is an increase of at least 10%, at least 25%, at least 75%, at least 100%, at least 125%, at least 150%, at least 175%, at least 200%, at least 250%, at least 300%, at least 400%, at least 500%, at least 600%, at least 700%, at least 800%, at least 900%, or at least 1000% as compared to T cell infiltration prior to administration or administration with a placebo.

In some aspects, administration of the compound of Formula (I) or a pharmaceutically acceptable salt thereof, such as a besylate salt thereof, and CPI therapy (which can be anti-PD1 therapy, and/or an anti-PDLI therapy), results in infiltration of T cells in tumors that are diagnostic positive for "cold" tumors, wherein the T cell infiltration is an increase of about 10%, about 25%, about 75%, about 100%, about 125%, about 150%, about 175%, about 200%, about 250%, about 300%, about 400%, about 500%, about 600%, about 700%, about 800%, about 900%, or about 1000% as compared to T cell infiltration prior to administration or administration with a placebo.

In some aspects, administration of the compound of Formula (I) or a pharmaceutically acceptable salt thereof, such as a besylate salt thereof, and a CPI therapy, which can be an anti-PD1 therapy and/or an anti-PDLI therapy, results in an inhibition of tumor growth. In some aspects, an inhibition of tumor growth is a decrease in a rate of tumor growth, a complete inhibition of tumor growth, a decrease in the spread of tumors, and/or a complete inhibition of the spread of tumors.

In some aspects, administration of the compound of Formula (I) or a pharmaceutically acceptable salt thereof, such as a besylate salt thereof, and a CPI therapy, which can be an anti-PD1 therapy and/or an anti-PDLI therapy, results in a reduction in tumor size. In some aspects, administration of the compound of Formula (I) or a pharmaceutically acceptable salt thereof, such as a besylate salt thereof, and a CPI therapy, which can be an anti-PD1 therapy and/or an anti-PDLI therapy, results in a reduction in tumor size by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some aspects, administration of the compound of Formula (I) or a pharmaceutically acceptable salt thereof, such as a besylate salt thereof, and a CPI therapy, which can be an anti-PD1 therapy and/or an anti-PDLI therapy, results in a reduction in tumor size by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

In some aspects, administration oft the compound of Formula (I) or a pharmaceutically acceptable salt thereof, such as a besylate salt thereof, and a CPI therapy, which can be an anti-PD1 therapy and/or an anti-PDLI therapy, results in a reduction in tumor size by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some aspects, administration of the compound of Formula (I) or a pharmaceutically acceptable salt thereof, such as a besylate salt thereof, is concurrently treated with a therapeutically effective amount of at least one CPI therapy, which can be an anti-PDL1 and/or anti-PD1 therapy.

In some aspects, the patient is concurrently treated with a therapeutic amount of the compound of Formula (I) or a pharmaceutically acceptable salt thereof, such as a besylate salt thereof, and a therapeutically effective amount of at least one CPI therapy, which can be an anti-PDL1 and/or anti-PDI therapy.

In some aspects, the patient is sequentially treated with a therapeutic amount of the compound of Formula (I) or a pharmaceutically acceptable salt thereof, such as a besylate salt thereof, and a therapeutically effective amount of at least one CPI therapy, which can be an anti-PDL1 and/or anti-PDI therapy.

In some aspects, the composition comprising the compound of Formula (I) or a pharmaceutically acceptable salt thereof, such as a besylate salt thereof, additionally comprises at least one CPI therapy, which can be an anti-PDL1 and/or anti-PD1 therapy.

In some aspects, the combination of treatment with a composition comprising (i) a therapeutically effective amount of the compound of Formula (I) or a pharmaceutically acceptable salt thereof, such as a besylate salt thereof, and (ii) at least one CPI therapy, which can be an anti-PDL1 and/or anti-PD1 therapy, results in an increase in survival of the patient and/or a slowing of tumor growth, as compared to administration of the composition comprising the compound of Formula (I) or a pharmaceutically acceptable salt thereof, such as a besylate salt thereof, or the CPI therapy alone.

In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in a slowing of the rate of tumor growth. In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in a slowing of the rate of tumor growth by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in a slowing of the rate of tumor growth by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in a slowing of the rate of tumor growth by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in the increase of the patient's survival by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to mean survival times exhibited with patients administered the composition alone and/or the CPI therapy alone.

In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in the increase of the patient's survival by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% as compared to mean survival times exhibited with patients administered the composition alone and/or the CPI therapy alone.

In some aspects, administration of the compound of Formula (I) or a pharmaceutically acceptable salt thereof, such as a besylate salt thereof, and a CPI therapy, which can be an anti-PD1 therapy and/or an anti-PDL1 therapy, results in the increase of the patient's survival by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to mean survival times exhibited with patients administered the composition alone and/or the CPI therapy alone.

In some aspects, the anti-PD1 therapy is selected from the group consisting of nivolumab, pembrolizumab, cemiplimab, spartalizumab, camrelizumab, sintilimab, tislelizumab, toripalimab, AMT-224, MEDI0680, durvalumab, and tislelizumab.

In some aspects, the anti-PDL1 therapy is selected from the group consisting of atezolizumab, avelumab, durvalumab, KN035, CK-301, CA-170, and BMS-986189.

In some aspects, the composition comprising the compound of Formula (I) or a pharmaceutically acceptable salt thereof, such as a besylate salt thereof, and a CPI therapy further comprises an effective amount of etoposide.

In some aspects, the administration to a patient in need thereof of a composition comprising the compound of Formula (I) or a pharmaceutically acceptable salt thereof, such as a besylate salt thereof, and a CPI therapy, which can be an anti-PD1 therapy and/or an anti-PDL1 therapy, further comprises administering an effective amount of etoposide.

In some aspects, the composition comprising the compound of Formula (I) or a pharmaceutically acceptable salt thereof, such as a besylate salt thereof, and a CPI therapy, which can be an anti-PD1 therapy and/or an anti-PDL1 therapy, further comprises a therapeutically effective amount of a platin. In some aspects, the platin is selected from the group consisting of cisplatin, carboplatin, exaliplatin, nedaplatin, triplatin tetranitrate, phenanthriplantin, picoplatin, and satraplatin.

In some aspects, the patient administered the composition comprising the compound of Formula (I) or a pharmaceutically acceptable salt thereof, such as a besylate salt thereof, and a CPI therapy, which can be an anti-PD1 therapy and/or an anti-PDL1 therapy, has a cancer selected from the group consisting of lung cancer, small cell lung cancer (SCLC), lung squamous cell carcinoma (LUSC), head and neck squamous cell carcinoma (HNSC), HPV-negative head and neck squamous cell carcinoma (HNSC HPV neg), bladder carcinoma (BLCA), bladder urothelial carcinoma, melanoma, skin cutaneous melanoma (SKCM), breast cancer, triple negative breast cancer (TNBC), ovarian cancer (OV), stomach cancer, stomach adenocarcinoma (STAD), sarcomas (SARC), neuroendocrine tumors, advanced solid tumors, prostate cancer, and marginal zone lymphoma.

In some aspects, the patient administered the composition comprising the compound of Formula (I) or a pharmaceutically acceptable salt thereof, such as a besylate salt thereof, and a CPI therapy, which can be an anti-PD1 therapy and/or an anti-PDL1 therapy, has a cancer selected from the group consisting of melanoma, metastatic non-small cell lung cancer, head and neck squamous cell carcinoma, squamous cell lung cancer, renal cell carcinoma, Hodgkin's lymphoma, cutaneous squamous cell carcinoma (CSCC), patients with locally advanced CSCC who are not candidates for curative surgery or curative radiation, solid tumors and lymphomas, relapsed or refractory classical Hodgkin lymphoma, small cell lung cancer (SCLC), solid tumors and hematologic cancers.

In some aspects, the composition comprising the compound of Formula (I) or a pharmaceutically acceptable salt thereof, such as a besylate salt thereof, is administered at least once weekly.

In some aspects, (a) the patient is concurrently treated with a therapeutically effective amount of at least one CPI, which can be for example anti-PDL1 and/or anti-PD1 therapy; and/or (b) the patient is treated sequentially with the composition comprising the compound of Formula (I) or a pharmaceutically acceptable salt thereof, such as a besylate salt thereof, and at least one CPI, which can be an anti-PDL1 and/or anti-PD1 therapy; and/or (c) the composition comprising the compound of Formula (I) or a pharmaceutically acceptable salt thereof, such as a besylate salt thereof, additionally comprises at least one CPI, which can be an anti-PDL1 and/or anti-PD1 therapy.

In some aspects, the combination of treatment with a composition comprising (i) a therapeutically effective amount of the compound of Formula (I) or a pharmaceutically acceptable salt thereof, such as a besylate salt thereof, and (ii) at least one CPI, which can be an anti-PDL1 and/or anti-PD1 therapy, results in an increase in survival of the patient and/or a slowing of tumor growth, as compared to administration of the composition comprising Formula (I) or a pharmaceutically acceptable salt thereof, such as a besylate salt thereof, alone or the CPI alone.

In some aspects, the tumor growth is slowed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by any clinically recognized method.

In some aspects, the patient's survival is increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as compared to mean survival times exhibited with patients administered the composition alone and/or the CPI alone.

In some aspects, the composition comprising the compound of Formula (I) or a pharmaceutically acceptable salt thereof, such as a besylate salt thereof, is administered daily, every other day, every three days, every 4 days, every 5 days, every 6 days, once weekly, twice weekly, three times weekly, every other week, once monthly, twice monthly, three times monthly, four times monthly, every other month, every three months, every four months, every five months, every six months, or any other suitable dosing period.

In some aspects, the composition comprising the compound of Formula (I) or a pharmaceutically acceptable salt thereof, such as a besylate salt thereof, is administered in the form of a tablet, pill, sachet, or capsule. In some aspects, the composition comprising a compound of formula (I) or a pharmaceutically acceptable salt thereof is adapted for oral administration.

The dose of the composition comprising the compound of Formula (I) or a pharmaceutically acceptable salt thereof, such as a besylate salt thereof, differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

VII. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

The term "administering" as used herein includes prescribing for administration as well as actually administering, and includes physically administering by the subject being treated or by another.

As used herein, the phrase "diagnostic positive for one or more 'cold' tumors" refers to a tumor or a patient having a tumor as exhibiting one or more of the following indicia for "cold" tumors—increased RCOR2 expression, exhibits the interferon response gene signature, exhibits the proneural gene signature, and/or exhibits a decreased tumor immune cell infiltrate or exhibits no detectable tumor immune cell infiltrate.

As used herein, the "interferon response gene signature" refers to AC124319.1, ADAR, APOL6, ARID5B, ARL4A, AUTS2, B2M, BANK1, BATF2, BPGM, BST2, BTG1, C1R, C1S, CASP1, CASP3, CASP4, CASP7, CASP8, CCL2, CCL5, CCL7, CD274, CD38, CD40, CD69, CD74, CD86, CDKN1A, CFB, CFH, CIITA, CMKLR1, CMPK2, CMTR1, CSF2RB, CXCL10, CXCL11, CXCL9, DDX58, DDX60, DHX58, EIF2AK2, EIF4E3, EPSTI1, FAS, FCGR1A, FGL2, FPR1, GBP4, GBP6, GCH1, GPR18, GZMA, HELZ2, HERC6, HIF1A, HLA-A, HLA-B, HLA-DMA, HLA-DQA1, HLA-DRB1, HLA-G, ICAM1, IDO1, IFI27, IFI30, IFI35, IFI44, IFI44L, IFIH1, IFIT1, IFIT2, IFIT3, IFITM2, IFITM3, IFNAR2, IFL10RA, IL15, IL15RA, IL18BP, IL2RB, IL4R, IL6, IL7, IRF1, IRF2, IRF4, IRF5, IRF7, IRF8, IRF9, ISG15, ISG20, ISOC1, ITGB7, JAK2, KLRK1, LAP3, LATS2, LCP2, LGALS3BP, LYSE, LYSMD2, 1-MAR, METTL7B, MT2A, MEHFD2, MVP, MX1, MX2, MYD88, NAMPT, NCOA3, NFKB1, NFKBIA, NLRC5, NMI, NOD1, NUP93, OAS2, OAS3, OASL, OGFR, P2RY14, PARP12, PARP14, PDE4B, PELI1, PFKP, PIM1, PLA2G4A, PLSCR1, PML, PNP, PNPT1, PSMA2, PSMA3, PSMB10, PSMB2, PSMB8, PSMB9, PSME1, PSME2, PTGS2, PTPN1, PTPN2, PTPN6, RAPGEF6, RBCK1, RIPK1, RIPK2, RNF31, RSAD2, RTP4, SAMD9L, SAMHD1, SECTM1, SELP, SERPING1, SLAMF7, SLC25A28, SOCS1, SOCS3, SOD2, SP110, SPPL2A, SRI, SSPN, ST3GAL5, ST8SIA4, STAT1, STAT2, STAT3, STAT4, TAP1, TAPBP, TDRD7, TNFAIP2, TNFAIP3, TNFAIP6, TNFAIP10, TOR1B, TRAFD1, TRIM14, TRIM 21, TRIM25, TRIM 26, TXNIP, UBE2L6, UPP1, USP18, VAMP5, VAMP8, VCAM1, WARS, XAF1, XCL1, ZBP1, and ZNFX1.

As used herein, the "interferon response signature subset A" refers to B2M, APOL6, CD86, IL15, IRF1, LCP2, CASP1, PSMB10, HLA-DMA, CD74, IL15RA, HLA-DRB1, FGL2, HLA-B, KLRK1, IL7, STAT4, CIITA, IL10RA, and SAMD9L.

As used herein, the "proneural gene signature" or "proneural signature" refers interchangeably to the list of 105 genes and the list of 141 genes described herein. If referring to a particular list, the "105 gene list" or the "141 gene list" will be specified.

The proneural signature 105 gene list is as follows: K056486, NKAIN1, FAM183A, SAMD13, LINC00622, CHRNB2, MEX3A, IGSF9, C1ORF192, CCDC181, OCLM, PPFIA4, PANK1, B4GALNT4, GAS2, MS4A8, MYRF, RCOR2, FLRT1, AK313893, NXPH4, BC073932, MSI1, CCDC169, FREM2, ATP7B, AF339817, AK124233, GPX2, PAR5, PLA2G4F, IGDCC3, GOLGA6L10, UBE2Q2P2, WDR93, PDIA2, CASKIN1, AK096982, TOX3, AK057689, C16ORF3, AK127378, EFNB3, DNAH2, ANKRD13B, SOCS7, RAMP2-AS1, FAM171A2, ADAM11, METAZOA_SRP_75, CBX2, ZNF850, LOC100379224, TTYH1, VN1R1, MEIS1-AS3, LONRF2, BCO22892, KLHL23, AX747067, CCDC108, IRS1, KIF1A, FLRT3, SIM2, IGSF5, CECR5-AS1, FAM227A, AX747137, FGD5P1, ACVR2B, LOC646903, FGFR3, FLJ13197, SLC10A4, TTC23L, MCIDAS, GUSBP9, GPR98, SEMA6A, PCDHGC4, USP49, TMEM151B, AK125212, PACRG, AK123300, COL28A1, SOSTDC1, AK098769, FKBP6, DPY19L2P4, EPO, CTTNBP2, KIAA1549, TAS2R5, FAM86B2, DQ595103, CHD7, AK094577, WNK2, TMEFF1, AL390170, MUM1L1, HS6ST2, and PNCK.

The proneural signature 141 gene list is as follows: CASKIN1, CBX2, CHD7, CHRNB2, CHRNG, EFNB3, FREM2, KCNMB2, KDM1A, KDMSB, KIAA1549, KIF1A, LRP4, MEX3A, MSI1, NKAIN1, ONECUT2, OTUD3, RCOR2, RIMKLA, SBK1, SOCS7, TET3, TMEFF1, WNK2, ACVR2B, ADAM11, ADAMTS20, ALX3, ANKRD13B, ATP7B, B4GALNT4, C16orf3, C1orf192, CCDC108, CCDC150, CCDC169, CCDC181, CDH8, CECR2, CENPV, CNTNAP5, COL28A1, COL6A4P1, CTTNBP2, DNAH2, DNAJB7, EPO, FAM171A2, FAM183A, FAM227A, FAM84A, FAM86B2, FGD5P1, FGF12, FGFR3, FKBP6, FLJ13197, FLRT1, FLRT3, FSIP2, GAS2, GDF11, GOLGA6L10, GPR125, GPR98, GPX2, GUSBP9, HOXC13, HS6ST2, IGDCC3, IGSF11, IGSF5, IGSF9, INA, IRS1, ISM2, KC6, KIAA1804, KLHL11, KLHL23, LINC00470, LINC00622, LOC100379224, LOC100631378, LOC148709, LOC641515, LOC646903, LONRF2, LPHN3, MCIDAS, MED12L, MS4A8, MUM1L1, MYRF, NKPD1, NRG4, NXPH4, OCLM, PACRG, PANK1, PAR5, PARD6G, PCDHB11, PCDHGA1, PCDHGC4, PDIA2, PGAP1, PIANP, PLA2G4F, PLCB1, PLCE1, PNCK, PPFIA4, PPM1L, SAMD13, SEMA6A, SERPINB12, SIM2, SLC10A4, SLC30A10, SLC9A4, SLCO1A2, SOSTDC1, STOX2, SYT14, SYT2, TAS2R5, TMEM151B, TOX3, TRIM45, TTC23L, TTYH1, UBE2Q2P2, USP49, VN1R1, WDR72, WDR93, ZBTB12, ZNF663, and ZNF850.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder.

The term "4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile" refers to the compound of Formula (I), which has the following structure

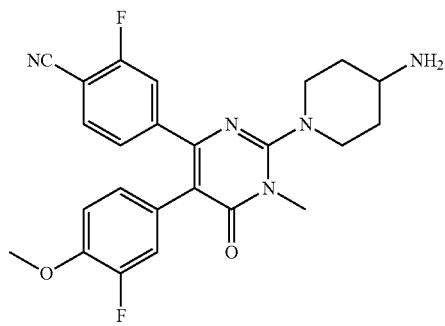 [SMILES: COc1ccc(-c2c(-c3ccc(C#N)c(F)c3)nc(N3CCC(N)CC3)n(C)c2=O)cc1F]

The compound of Formula (I) is described in U.S. patent application Ser. No. 9,255,097.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogen-phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge S. M. et al., *Pharmaceutical Salts*, J. Pharma. Sci. 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

As used herein, the "non-synonymous mutational burden" is the total number of non-synonymous mutated bases in the tumor genome from the patient/subject divided by the Mb of the genome covered. A high or low non-synonymous mutational burden is determined relative to the non-synonymous mutational burdens of other patients/subjects having the same type or classification of tumor. Thus, the determination of high and low is relative to an experimental/clinical control. See Fernandez et al., (2019), *JCO Precis Oncol*, 3:10.1200/P0/18.00400).

EXAMPLES

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1

The purpose of this example was to describe preparation of 4-[2-(4-amino-piperidin-1-yl)-5-(3-fluoro-4-methoxyphenyl)-1-methyl-6-oxo-1,6-dihydro-pyrimidin-4-yl]-2-fluoro-benzonitrile (compound of Formula (I)), which has the following structure:

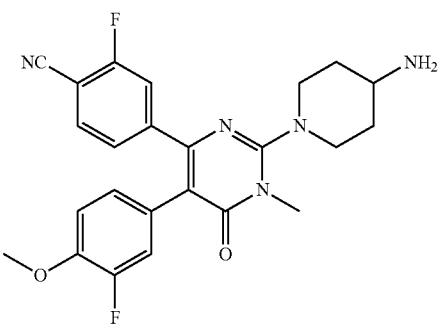

To a solution of tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate (5.2 g, 9.44 mmol) in EA (20 mL) was added a 1N HCl in EA (30 mL). The mixture was stirred at RT for 2 h. The solvent was concentrated in vacuo to give the title product as the HCl salt (4.05 g, 88%). $^1$H NMR (400 MHz, CD$_3$OD): δ 1.77-1.79 (m, 2H), 2.02-2.04 (m, 2H), 2.99-3.04 (m, 2H), 3.26-3.00 (m, 1H), 3.38 (s, 3H), 3.73 (s, 3H), 3.73-3.75 (m, 2H), 6.67-6.68 (m, 1H), 6.84-6.95 (m, 2 H), 7.12-7.14 (m, 1H), 7.24-7.36 (m, 1H), 7.46-7.50 (m, 1H). [M+H] Calc'd for C$_{24}$H$_{23}$F$_2$N$_5$O$_2$, 452; Found, 452.

Example 2: T Cell Exclusion Signature and RCOR2 as a Cold Tumor Biomarker

The purpose of this example was to evaluate the ability of RCOR2 to function as a cold tumor biomarker. Such a marker can be used in targeting RCOR2 expression in methods of treating cancer.

RNA-Seq data was used to identify genes associated with T Cell Exclusion (TCE) ("Cold") tumors. Tumor types with a range of hot and cold tumor samples, varying response rates to IO therapy, and a high number of patients in the data set were utilized—Ovarian (OV, n=430); Bladder (BLCA, n=411); and Melanoma (SKCM, n=368). Within each tumor type, samples were ranked by the expression of the single gene CD8A, and divided into quartiles with 1$^{st}$ (lowest expression) being labelled cold and 4$^{th}$ (highest expression) being labeled hot.

Differential gene expression analysis between the 1$^{st}$ and 4$^{th}$ quartiles of samples identified two sets of genes for each tumor type. Hot genes—e.g., genes with significantly higher expression in hot samples (High CD8A) and Cold genes—e.g., genes with significantly higher expression in cold samples (low CD8A). Pathway and gene signature analysis was performed for each gene list, and there was a 105 proneural T cell exclusion gene signature shared across multiple tumor types. Thus, across all three tumor types (OV, BLCA, and SKCM), a core 105 proneural gene signature was identified.

The 105 proneural gene signature includes the following 105 genes: AK056486, NKAIN1, FAM183A, SAMD13, LINC00622, CHRNB2, MEX3A, IGSF9, C1ORF192, CCDC181, OCLM, PPFIA4, PANK1, B4GALNT4, GAS2, MS4A8, MYRF, RCOR2, FLRT1, AK313893, NXPH4, BC073932, MSI1, CCDC169, FREM2, ATP7B, AF339817, AK124233, GPX2, PAR5, PLA2G4F, IGDCC3, GOLGA6L10, UBE2Q2P2, WDR93, PDIA2, CASKIN1, AK096982, TOX3, AK057689, C16ORF3, AK127378, EFNB3, DNAH2, ANKRD13B, SOCS7, RAMP2-AS1, FAM171A2, ADAM11, METAZOA_SRP_75, CBX2, ZNF850, LOC100379224, TTYH1, VN1R1, MEIS1-AS3, LONRF2, BCO22892, KLHL23, AX747067, CCDC108, IRS1, KIF1A, FLRT3, SIM2, IGSF5, CECR5-AS1, FAM227A, AX747137, FGD5P1, ACVR2B, LOC646903, FGFR3, FLJ13197, SLC10A4, TTC23L, MCIDAS, GUSBP9, GPR98, SEMA6A, PCDHGC4, USP49, TMEM151B, AK125212, PACRG, AK123300, COL28A1, SOSTDC1, AK098769, FKBP6, DPY19L2P4, EPO, CTTNBP2, KIAA1549, TAS2R5, FAM86B2, DQ595103, CHD7, AK094577, WNK2, TMEFF1, AL390170, MUM1L1, HS6ST2, and PNCK.

The 105 proneural gene signature is similar to the proneural gene signature in glioblastoma (GBM), which includes 175 proneural genes. A subset of the cold cell lines had high expression of the proneural signature and low expression of interferon response genes. The interferon response genes included: AC124319.1, ADAR, APOL6, ARID5B, ARL4A, AUTS2, B2M, BANK1, BATF2, BPGM, BST2, BTG1, C1R, C1S, CASP1, CASP3, CASP4, CASP7, CASP8, CCL2, CCL5, CCL7, CD274, CD38, CD40, CD69, CD74, CD86, CDKN1A, CFB, CFH, CIITA, CMKLR1, CMPK2, CMTR1, CSF2RB, CXCL10, CXCL11, CXCL9, DDX58, DDX60, DHX58, EIF2AK2, EIF4E3, EPSTI1, FAS, FCGR1A, FGL2, FPR1, GBP4, GBP6, GCH1, GPR18, GZMA, HELZ2, HERC6, HIF1A, HLA-A, HLA-B, HLA-DMA, HLA-DQA1, HLA-DRB1, HLA-G, ICAM1, IDO1, IFI27, IFI30, IFI35, IFI44, IFI44L, IFIH1, IFIT1, IFIT2, IFIT3, IFITM2, IFITM3, IFNAR2, IFL10RA, IL15, IL15RA, IL18BP, IL2RB, IL4R, IL6, IL7, IRF1, IRF2, IRF4, IRF5, IRF7, IRF8, IRF9, ISG15, ISG20, ISOC1, ITGB7, JAK2, KLRK1, LAP3, LATS2, LCP2, LGALS3BP, LYSE, LYSMD2, 1-MAR, METTL7B, MT2A, MEHFD2, MVP, MX1, MX2, MYD88, NAMPT, NCOA3, NFKB1, NFKBIA, NLRC5, NMI, NOD1, NUP93, OAS2, OAS3, OASL, OGFR, P2RY14, PARP12, PARP14, PDE4B, PELI1, PFKP, PIM1, PLA2G4A, PLSCR1, PML, PNP, PNPT1, PSMA2, PSMA3, PSMB10, PSMB2, PSMB8, PSMB9, PSME1, PSME2, PTGS2, PTPN1, PTPN2, PTPN6, RAPGEF6, RBCK1, RIPK1, RIPK2, RNF31, RSAD2, RTP4, SAMD9L, SAMHD1, SECTM1, SELP, SERPING1, SLAMF7, SLC25A28, SOCS1, SOCS3, SOD2, SP110, SPPL2A, SRI, SSPN, ST3GAL5, ST8SIA4, STAT1, STAT2, STAT3, STAT4, TAP1, TAPBP, TDRD7, TNFAIP2, TNFAIP3, TNFAIP6, TNFAIP10, TOR1B, TRAFD1, TRIM14, TRIM 21, TRIM25, TRIM 26, TXNIP, UBE2L6, UPP1, USP18, VAMP5, VAMP8, VCAM1, WARS, XAF1, XCL1, ZBP1, and ZNFX1.

RCOR2 was found to be the most highly correlated with T cell Exclusion genes across cold tumor types. In addition, with regard to normal tissue, RCOR2 exhibited the highest expression in the brain, specifically the cortex, with particularly high expression in proneural glioblastoma. Finally, RCOR2-LSD1 complex is known to regulate histone H3 lysine 4 demethylation.

An evaluation of RCOR2 and the proneural signature led to the identification of RCOR2 and the proneural signature as anti-correlated with T cell infiltration in the IFNG response.

Example 3: RCOR2 and the Proneural T Cell Signature in Small Cell Lung Cancer (SCLC)

The purpose of this example is to evaluate the ability to target RCOR2 and the proneural T cell signature in small cell lung cancer (SCLC) as a method of optimizing effective cancer treatment.

Figure 9A:
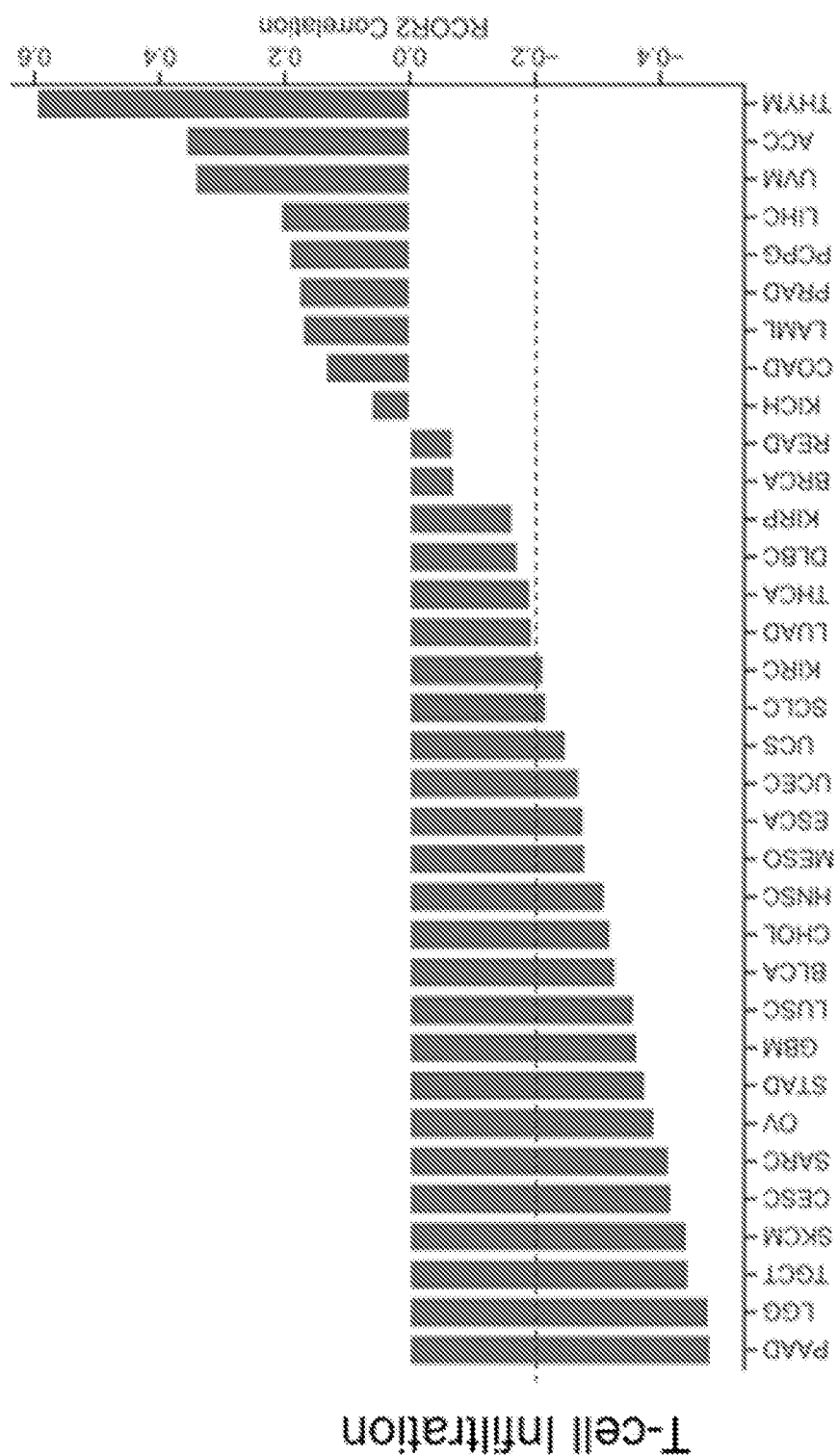
FIGS. 9A and B show that across various tumor tissue types (including SCLC), RCOR2 is anti-correlated with T-cell infiltration (FIG. 9A) and IFNG Response (FIG. 9B).
Figure 9B:
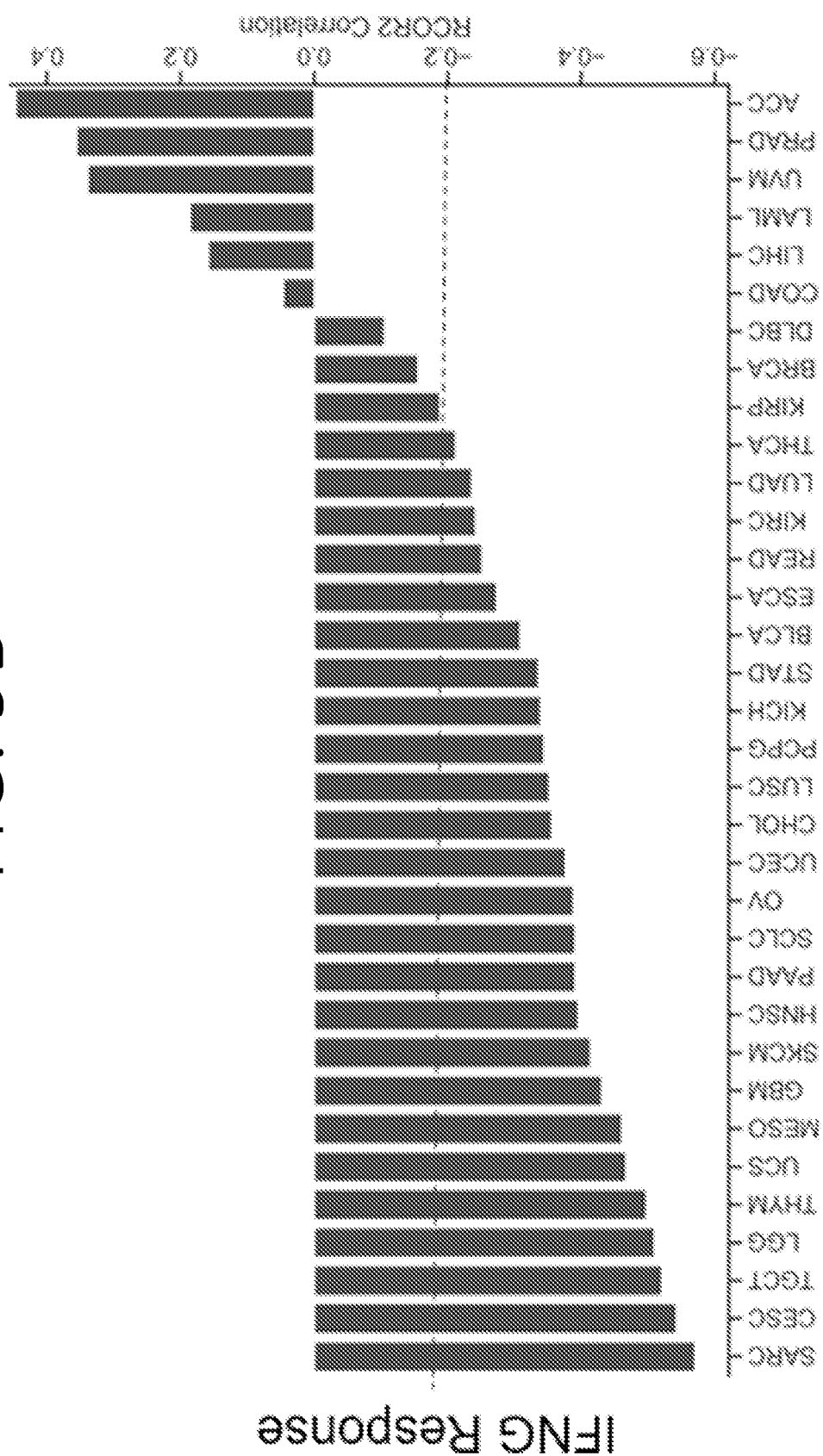
Figure 10A:
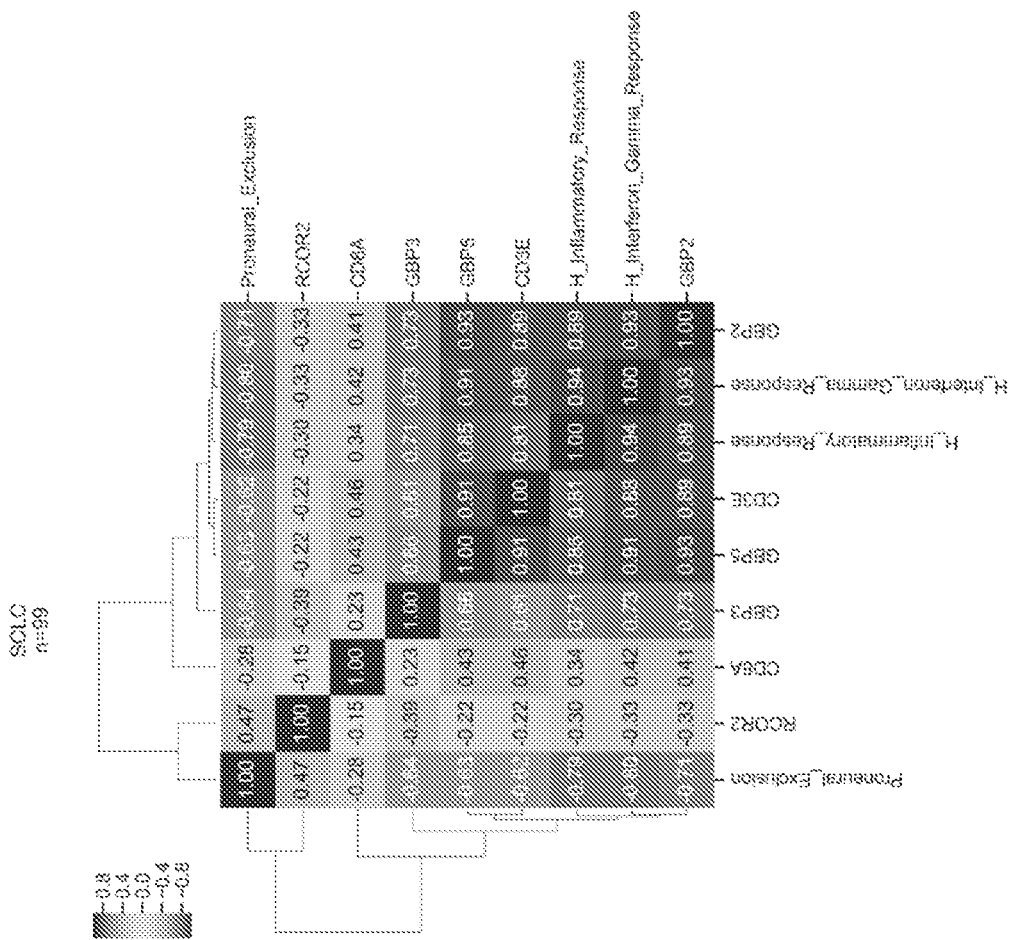
FIGS. 10A, B, and C shows graphs of proneural signature and IFNγ response in three types of cancer: SCLC (n=99) (FIG. 10A), OV (n=430) (FIG. 10B), and LUSC (n=501) (FIG. 10C). These heat maps depict correlations (negative and positive) with various gene signatures and genes compared with one another. The strongest negative correlations in the figures are between the proneural signature genes and the immune signatures of IFNG response and inflammatory response.
Figure 10B:
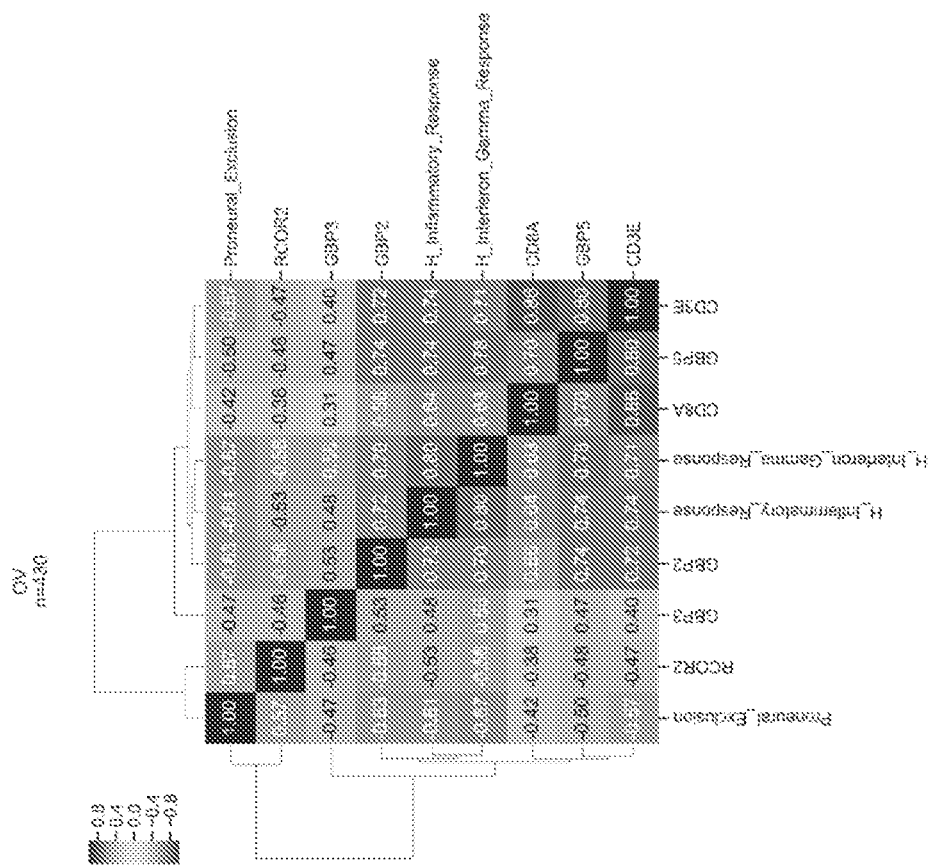
Figure 10C:
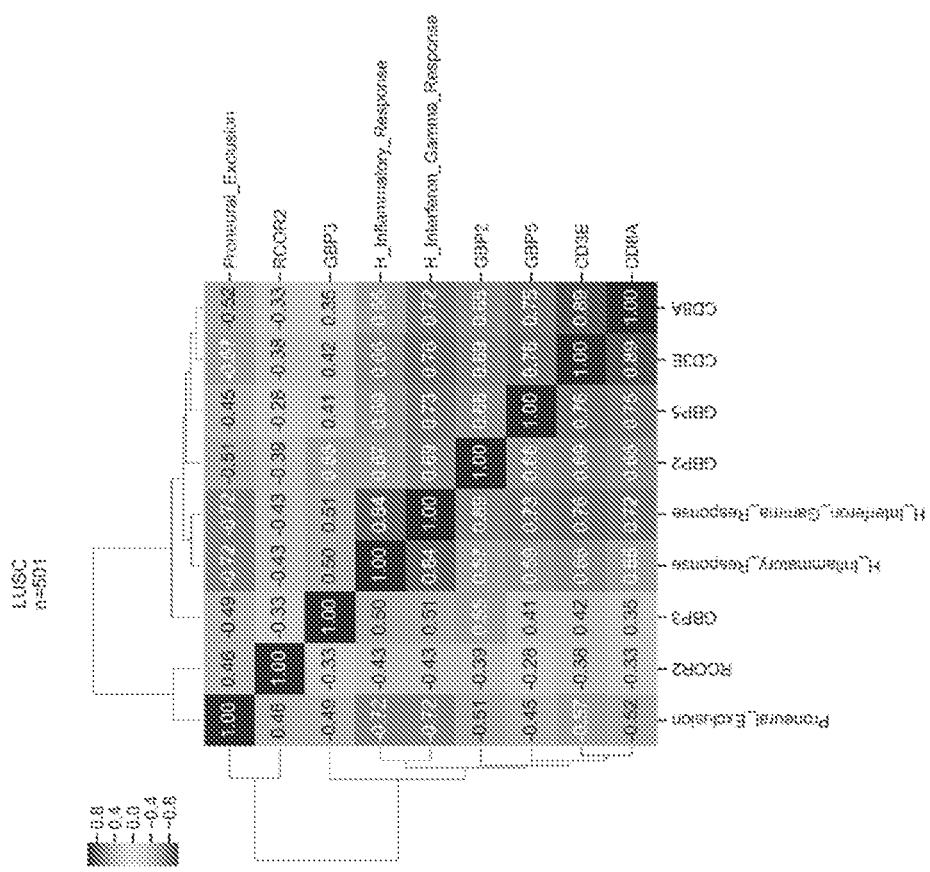

In small cell lung cancer, RCOR2 is anti-correlated with T cell infiltration (FIG. 9A) and interferon gamma (IFNG or IFNγ) response (FIG. 9B). In a heatmap identifying expression correlations in SCLC, the proneural signature and RCOR2 exhibited a strong anti-correlation with the IFNγ response (FIG. 10A), and the proneural signature score generally shows indicates a more robust relationship than just RCOR2 alone.

Figure 11:
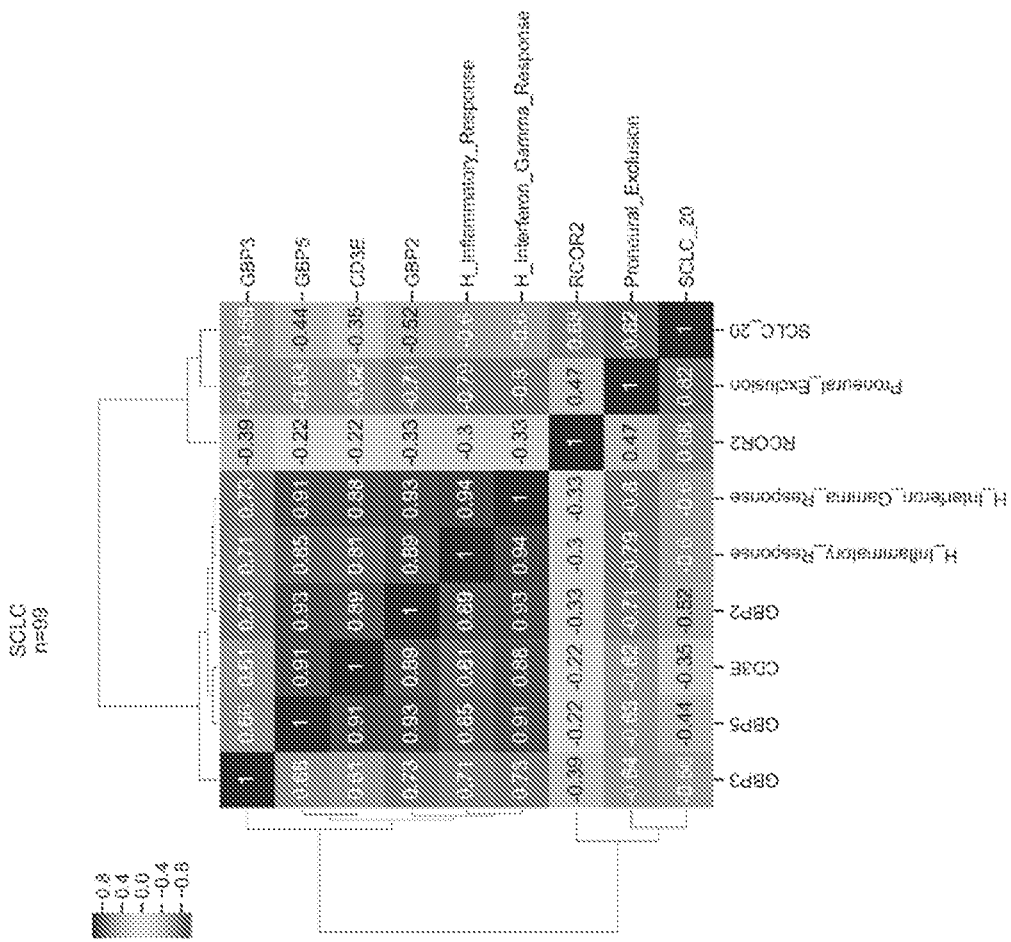
FIG. 11 is a heat map that depicts correlations (negative and positive) with various gene signatures and genes compared with one another in SCLC. This figure differs from FIG. 10A in that it includes a score labeled SCLC 20 which is derived using a subset of 20 genes of the larger 105 gene proneural signature. It exhibits a stronger negative correlation vs the immune pathways (inflammatory response and IFNG response) than RCOR2 by itself with those immune pathways. As a reference, it also shows that the 105 gene proneural signature has the strongest negative correlation with immune pathways. These 20 genes are represented by "SCLC_20" and these are 20 genes co-expressed with RCOR2.

A subset of the exclusion signature based on RCOR2 co-expressed genes has a stronger anti-correlation than just RCOR2 alone (FIG. 11). This reduced signature consists of RCOR2, NKAIN1, MSI1, CBX2, IGDCC3, GPC2, CECR2, KLHL23, TMEFF1, MEX3A, KIAA1549, FAM171A2, CENPV, INA, TMEM151B, KIF1A, SYT14, ONECUT2, KDM1A, and CHRNB2.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

What is claimed is:

1. A method of treating cancer in a subject in need thereof, the method comprising:
   (a) identifying a patient having a cancer tumor that is a diagnostic positive cold tumor; and
   (b) administering to the patient a composition comprising a therapeutically effective amount of a compound having the structure of Formula (I), or a pharmaceutically acceptable salt thereof,

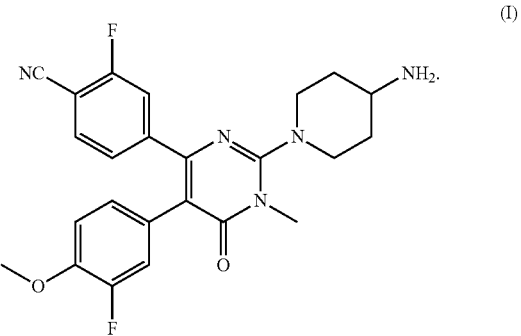 [SMILES: COc1ccc(-c2c(-c3ccc(C#N)c(F)c3)nc(N3CCC(N)CC3)n(C)c2=O)cc1F]

wherein the diagnostic positive cold tumor exhibits a cold tumor signature as defined by
   (a) low or no CD8 T cell infiltration within the tumor; and/or
   (b) exhibition of T cell non-inflamed or T cell excluded based on the presence of T cells within the tumor; and/or
   (c) the presence of T cells within the tumor is measured or estimated by gene expression levels of T cell markers in bulk RNA profiling data, and
wherein the patient's cancer cells exhibit a decrease in the gene expression of one or more interferon response genes, wherein the decrease in the gene expression is relative to the gene expression of a control gene.

2. The method of claim 1, wherein the patient:
   (a) has failed single checkpoint inhibitor (CPI) therapy, has minimal response to CPI therapy, or no therapeutic effect is observed for CPI therapy; and
   (b) cells of the tumor display a high gene expression of REST Corepressor 2 (RCOR2) relative to the median RCOR2 gene expression of tumors in other patients having the same tumor type.

3. The method of claim 1, wherein the patient:
   (a) is naïve to a CPI therapy; and
   (b) cells of the tumor display a high gene expression of RCOR2 relative to the median RCOR2 gene expression of tumors in other patients having the same tumor type.

4. The method of claim 2, wherein:
   (a) high gene expression of RCOR2 is in the top 25% of expression of tumors in other patients having the same tumor type; or
   (b) high gene expression of RCOR2 is in the top 10% of expression of tumors in other patients having the same tumor type.

5. The method of claim 2, wherein:
   (a) the CPI therapy comprises anti-programmed cell death protein 1 (PD1) and/or programmed death-ligand 1 (PD-L1) therapy; and
   (b) the patient's cancer cells display a high gene expression of REST Corepressor 2 RCOR2).

6. The method of claim 1, wherein:
the patient's cancer cells display a high gene expression of RCOR2.

7. The method of claim 1, wherein:
   (a) the patient's cancer cells exhibit an increase in the gene expression of one or more of the following genes: AK056486, NKAIN1, FAM183A, SAMD13, LINC00622, CHRNB2, MEX3A, IGSF9, C1ORF192, CCDC181, OCLM, PPFIA4, PANK1, B4GALNT4, GAS2, MS4A8, MYRF, RCOR2, FLRT1, AK313893, NXPH4, BC073932, MSI1, CCDC169, FREM2, ATP7B, AF339817, AK124233, GPX2, PAR5, PLA2G4F, IGDCC3, GOLGA6L10, UBE2Q2P2, WDR93, PDIA2, CASKIN1, AK096982, TOX3, AK057689, C16ORF3, AK127378, EFNB3, DNAH2, ANKRD13B, SOCS7, RAMP2-AS1, FAM171A2, ADAM11, METAZOA_SRP_75, CBX2, ZNF850, LOC100379224, TTYH1, VN1R1, MEIS1-AS3, LONRF2, BC022892, KLHL23, AX747067, CCDC108, IRS1, KIF1A, FLRT3, SIM2, IGSF5, CECR5-AS1, FAM227A, AX747137, FGD5P1, ACVR2B, LOC646903, FGFR3, FLJ13197, SLC10A4, TTC23L, MCIDAS, GUSBP9, GPR98, SEMA6A, PCDHGC4, USP49, TMEM151B, AK125212, PACRG, AK123300, COL28A1, SOSTDC1, AK098769, FKBP6, DPY19L2P4, EPO, CTTNBP2, KIAA1549, TAS2R5, FAM86B2, DQ595103, CHD7, AK094577, WNK2, TMEFF1, AL390170, MUM1L1, HS6ST2, and PNCK; and (b) the increase in the gene expression is relative to the gene expression of a control gene.

8. The method of claim 7, wherein the patient's cancer cells:
(a) exhibit an increase in the gene expression of at least about 10% or at least about 15% of the genes where expression levels are measured; or
(b) exhibit an increase in the gene expression of at least about 20%, at least about 25%, at least about 30%, or at least about 35% of the genes where expression levels are measured; or
(c) exhibit an increase in the gene expression of at least about 40%, at least about 45%, at least about 50%, or at least about 55% of the genes where expression levels are measured; or
(d) exhibit an increase in the gene expression of at least about 60%, at least about 65%, at least about 70%, or at least about 75% of the genes where expression levels are measured; or
(e) exhibit an increase in the gene expression of at least about 80% of the genes where expression levels are measured.

9. The method of claim 1, wherein:
the patient's cancer cells exhibit a decrease in the gene expression of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the interferon response genes where expression levels are measured, and wherein the decrease in the gene expression is relative to the gene expression of a control gene.

10. The method of claim 1, wherein the interferon response genes are selected from: AC124319.1, ADAR, APOL6, ARID5B, ARL4A, AUTS2, B2M, BANK1, BATF2, BPGM, BST2, BTG1, CIR, CIS, CASP1, CASP3, CASP4, CASP7, CASP8, CCL2, CCL5, CCL7, CD274, CD38, CD40, CD69, CD74, CD86, CDKNIA, CFB, CFH, CIITA, CMKLR1, CMPK2, CMTR1, CSF2RB, CXCL10, CXCL11, CXCL9, DDX58, DDX60, DHX58, EIF2AK2, EIF4E3, EPSTI1, FAS, FCGRIA, FGL2, FPR1, GBP4, GBP6, GCH1, GPR18, GZMA, HELZ2, HERC6, HIFIA, HLA-A, HLA-B, HLA-DMA, HLA-DQA1, HLA-DRB1, HLA-G, ICAM1, IDO1, IFI27, IFI30, IFI35, IFI44, IFI44L, IFIH1, IFIT1, IFIT2, IFIT3, IFITM2, IFITM3, IFNAR2, IFL10RA, IL15, IL15RA, IL18BP, IL2RB, IL4R, IL6, IL7, IRF1, IRF2, IRF4, IRF5, IRF7, IRF8, IRF9, ISG15, ISG20, ISOC1, ITGB7, JAK2, KLRK1, LAP3, LATS2, LCP2, LGALS3BP, LYSE, LYSMD2, 1-MAR, METTL7B, MT2A, MEHFD2, MVP, MX1, MX2, MYD88, NAMPT, NCOA3, NFKB1, NFKBIA, NLRC5, NMI, NOD1, NUP93, OAS2, OAS3, OASL, OGFR, P2RY14, PARP12, PARP14, PDE4B, *PELI*1, PFKP, PIM1, PLA2G4A, PLSCR1, PML, PNP, PNPT1, PSMA2, PSMA3, PSMB10, PSMB2, PSMB8, PSMB9, PSME1, PSME2, PTGS2, PTPN1, PTPN2, PTPN6, RAPGEF6, RBCK1, RIPK1, RIPK2, RNF31, RSAD2, RTP4, SAMD9L, SAMHD1, SECTM1, SELP, SERPING1, SLAMF7, SLC25A28, SOCS1, SOCS3, SOD2, SP110, SPPL2A, SRI, SSPN, ST3GAL5, ST8SIA4, STAT1, STAT2, STAT3, STAT4, TAP1, TAPBP, TDRD7, TNFAIP2, TNFAIP3, TNFAIP6, TNFAIP10, TORIB, TRAFD1, TRIM14, TRIM 21, TRIM25, TRIM 26, TXNIP, UBE2L6, UPP1, USP18, VAMP5, VAMP8, VCAM1, WARS, XAF1, XCL1, ZBP1, and ZNFX1.

11. The method of claim 1, wherein:
(a) the compound of Formula (I) or a pharmaceutically acceptable salt thereof is an inhibitor of Lysine-specific histone demethylase 1 (LSD-1); and/or
(b) the compound of Formula (I) or a pharmaceutically acceptable salt thereof is a reversible antagonist to LSD-1; and/or
(c) the compound of Formula (I) or a pharmaceutically acceptable salt thereof is a reversible inhibitor of LSD-1.

12. The method of claim 11, wherein:
(a) when LSD-1 is blocked, infiltration of T cells is thereby enabled, thus allowing anti-PDL1 and/or anti-PD1 therapy to retard tumor growth and/or reduce tumor size; and/or
(b) LSD-1 is inhibited from demethylating histone complexes, and thereby infiltration of T cells is enabled, thus allowing anti-PDL1 and/or anti-PD1 therapy to retard tumor growth and/or tumor size; and/or
(c) LSD-1 is prevented from forming a functional protein complex with RCOR2, and thereby infiltration of T cells is enabled, thus allowing anti-PDL1 and/or anti-PD1 therapy to retard tumor growth and/or tumor size.

13. The method of claim 1, wherein the subject's cancer has a high non-synonymous mutational burden.

14. The method of claim 1, wherein:
(a) the patient is concurrently treated with a therapeutically effective amount of at least one CPI therapy, which can be an anti-PDL1 and/or anti-PD1 therapy; and/or
(b) the patient is treated sequentially with the composition comprising the compound of Formula (I) or a pharmaceutically acceptable salt thereof, and at least one CPI therapy, which can be an anti-PDL 1 and/or anti-PD1 therapy; and/or
(c) the composition comprising the compound of Formula (I) or a pharmaceutically acceptable salt thereof, additionally comprises at least one CPI therapy, which can be an anti-PDL1 and/or anti-PD1 therapy.

15. The method of claim 14, wherein the combination of treatment with a composition comprising (i) a therapeutically effective amount of the compound of Formula (I) or a pharmaceutically acceptable salt thereof, and (ii) at least one CPI therapy, which can be an anti-PDL1 and/or anti-PD1 therapy, results in an increase in survival of the patient and/or a slowing of tumor growth, as compared to administration of the composition comprising the compound of Formula (I) or a pharmaceutically acceptable salt thereof alone or the CPI therapy alone; and optionally wherein
(a) tumor growth is slowed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by any clinically recognized method; and/or (b) the patient's survival is increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as compared to mean survival times exhibited with patients administered the composition alone and/or the anti-PDL1 and/or anti-PD1 therapy alone.

16. The method of claim 14, wherein the CPI therapy is an anti-PD1 therapy selected from the group consisting of:
    (a) nivolumab;
    (b) pembrolizumab;
    (c) cemiplimab;
    (d) spartalizumab;
    (e) camrelizumab;
    (f) sintilimab;
    (g) tislelizumab;
    (h) toripalimab;
    (i) AMP-224;
    (j) MEDI0680;
    (k) durvalumab; and
    (l) tislelizumab.

17. The method of claim 14, wherein the CPI therapy is an anti-PDL1 therapy selected from the group consisting of:
    (a) atezolizumab;
    (b) avelumab;
    (c) durvalumab;
    (d) KN035;
    (e) CK-301;
    (f) CA-170; and
    (g) BMS-986189.

18. The method of claim 1, wherein:
    (a) the composition further comprises a therapeutically effective amount of etoposide; or
    (b) an additional composition comprising a therapeutically effective amount of etoposide is administered.

19. The method of claim 1, wherein:
    (a) the composition further comprises a therapeutically effective amount of a platin, and optionally wherein the platin is selected from the group consisting of cisplatin, carboplatin, exaliplatin, nedaplatin, triplatin tetranitrate, phenanthriplantin, picoplatin, and satraplatin; or
    (b) an additional composition comprising a therapeutically effective amount of a platin is administered, and optionally wherein the platin is selected from the group consisting of cisplatin, carboplatin, exaliplatin, nedaplatin, triplatin tetranitrate, phenanthriplantin, picoplatin, and satraplatin.

20. The method of claim 1, wherein:
    (a) the patient has a cancer selected from the group consisting of: lung cancer, small cell lung cancer (SCLC), lung squamous cell carcinoma (LUSC), head and neck squamous cell carcinoma (HNSC), HPV-negative head and neck squamous cell carcinoma (HNSC HPV neg), bladder carcinoma (BLCA), bladder urothelial carcinoma, melanoma, skin cutaneous melanoma (SKCM), breast cancer, triple negative breast cancer (TNBC), ovarian cancer (OV), stomach cancer, stomach adenocarcinoma (STAD), sarcomas (SARC), glioma, neuroendocrine tumors, advanced solid tumors, prostate cancer, marginal zone lymphoma, pancreatic cancer, pancreatic adenocarcinoma (PAAD), pancreatic ductal adenocarcinoma (PDAC), pancreatic neuroendocrine tumors (PNET), low grade glioma (LGG), cervical squamous cell carcinoma and endocervical adenocarcinoma (CESC), testicular germ cell tumors (TGCT), kidney renal clear cell carcinoma (KIRC), kidney renal papillary cell carcinoma (KIRP), and esophageal carcinoma (ESCA); and/or
    (b) the patient has a cancer selected from the group consisting of melanoma, metastatic non-small cell lung cancer, head and neck squamous cell carcinoma, squamous cell lung cancer, renal cell carcinoma, Hodgkin's lymphoma, cutaneous squamous cell carcinoma (CSCC), patients with locally advanced CSCC who are not candidates for curative surgery or curative radiation, solid tumors and lymphomas, relapsed or refractory classical Hodgkin lymphoma, small cell lung cancer (SCLC), solid tumors and hematologic cancers.

21. The method of claim 1, wherein:
    (a) the composition comprising the compound of Formula (I) or a pharmaceutically acceptable salt thereof, is administered at least once weekly; and/or
    (b) the composition comprising the compound of Formula (I) or a pharmaceutically acceptable salt thereof, is administered daily, every other day, every 3 days, every 4 days, every 5 days, once weekly, twice weekly, three times weekly, every other week, or any other suitable dosing period.

22. The method of claim 1, wherein:
    (a) the compound of Formula (I) or a pharmaceutically acceptable salt thereof, is in the form of an injectable solution; or
    (b) the compound of Formula (I) or a pharmaceutically acceptable salt thereof is administered as an intravenous injection; or
    (c) the compound of Formula (I) or a pharmaceutically acceptable salt thereof, is adapted for oral administration.

* * * * *